United States Patent
Dunkel et al.

(10) Patent No.: US 8,017,558 B2
(45) Date of Patent: Sep. 13, 2011

(54) CARBOXAMIDES FOR CONTROLLING MICRO-ORGANISMS IN PLANT AND MATERIAL PROTECTION

(75) Inventors: Ralf Dunkel, Lyons (FR); Hans-Ludwig Elbe, Wuppertal (DE); Jörg Nico Greul, Leichlingen (DE); Herbert Gayer, Monheim (DE); Bernd-Wieland Krüger, Bergisch Gladbach (DE); Arnd Voerste, Köln (DE); Ulrike Wachendorff-Neumann, Neuwied (DE); Peter Dahmen, Neuss (DE)

(73) Assignee: Bayer Cropscience AG, Monheim (DE)

( * ) Notice: Subject to any disclaimer, the term of this patent is extended or adjusted under 35 U.S.C. 154(b) by 280 days.

(21) Appl. No.: 12/097,457

(22) PCT Filed: Dec. 5, 2006

(86) PCT No.: PCT/EP2006/011653
§ 371 (c)(1),
(2), (4) Date: Nov. 17, 2008

(87) PCT Pub. No.: WO2007/068377
PCT Pub. Date: Jun. 21, 2007

(65) Prior Publication Data
US 2009/0247586 A1  Oct. 1, 2009

(30) Foreign Application Priority Data
Dec. 17, 2005 (DE) .................. 10 2005 060 466

(51) Int. Cl.
| | |
|---|---|
| *A01N 43/36* | (2006.01) |
| *A01N 43/56* | (2006.01) |
| *A01N 43/76* | (2006.01) |
| *A01N 43/78* | (2006.01) |
| *A01N 43/08* | (2006.01) |
| *A01N 43/10* | (2006.01) |
| *A61K 31/34* | (2006.01) |
| *A61K 31/381* | (2006.01) |
| *A61K 31/415* | (2006.01) |
| *A61K 31/421* | (2006.01) |
| *A61K 31/426* | (2006.01) |
| *A61K 31/425* | (2006.01) |
| *A61K 31/433* | (2006.01) |
| *C07D 207/34* | (2006.01) |
| *C07D 231/14* | (2006.01) |
| *C07D 263/34* | (2006.01) |
| *C07D 275/03* | (2006.01) |
| *C07D 277/32* | (2006.01) |
| *C07D 285/06* | (2006.01) |
| *C07D 307/18* | (2006.01) |
| *C07D 333/26* | (2006.01) |

(52) U.S. Cl. ........ 504/361; 514/117; 514/365; 514/372; 514/374; 514/403; 514/427; 514/438; 514/461; 548/202; 548/214; 548/235; 548/566; 548/123; 548/375.1; 549/74; 549/491

(58) Field of Classification Search ................ None
See application file for complete search history.

(56) References Cited

U.S. PATENT DOCUMENTS

| | | | |
|---|---|---|---|
| 4,341,551 A * | 7/1982 | Kruger et al. ............. | 504/225 |
| 5,093,347 A | 3/1992 | Graneto et al. | |
| 5,330,995 A | 7/1994 | Eicken et al. | |
| 5,922,732 A | 7/1999 | Urch et al. | |
| 7,173,055 B1 | 2/2007 | Walter | |
| 2002/0061913 A1 | 5/2002 | Urch et al. | |
| 2006/0116414 A1 | 6/2006 | Dunkel et al. | |

FOREIGN PATENT DOCUMENTS

| | | |
|---|---|---|
| EP | 0545099 | 7/1992 |
| JP | 01290662 | 11/1989 |
| JP | 09132567 | 5/1997 |
| WO | 9637494 | 11/1996 |
| WO | 9825923 | 6/1998 |
| WO | 0142223 | 6/2001 |
| WO | 0238542 | 5/2002 |
| WO | 03070705 | 8/2003 |

OTHER PUBLICATIONS

Qiang, et al., Tetrahedron Letters, 29:3517 (1988).*
PCT/ISA/210 International Search Report of PCT/EP2006/011653 dated Feb. 26, 2007 (4 pages).
John S. Davidson; "A Preparation of 3-Amino-4,5-diaryl-1,2,4-triazoles", Synthesis, 1979, pp. 359-361, XP002421834.
Wolfgang Walter et al., "Tautomerie zwischen Thioamid-S-oxiden und Sulfensaeuren", Liebigs Annalen Der Chemie, Bd. 752, 1971, pp. 115-135, XP009079695.
Wolfgang Walter et al., "Ueber die Anisochronie der Methyl-Gruppen in ortho-isopropyl-substituierten Thioaniliden", Liebigs Annalen Der Chemie, Bd. 755, 1972, pp. 127-144, XP009079696.
PCT/IB/373 International Preliminary Report on Patentability of PCT/EP2006/011653, English and German, (18 pages), (Jun. 18, 2006).
PCT/IB/237 Written Opinion of the International Search Authroirty of PCT/EP2006/011653, English and German (16 pages, (Aug. 5, 2008).

* cited by examiner

*Primary Examiner* — Yong Chu
*Assistant Examiner* — Michael Barker
(74) *Attorney, Agent, or Firm* — Baker Donelson Bearman, Caldwell & Berkowitz, PC

(57) ABSTRACT

Novel carboxamides of the formula (I)

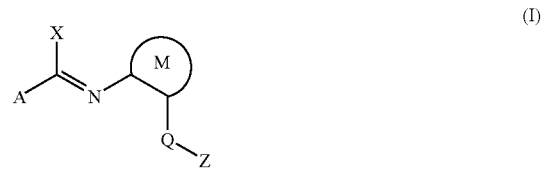

(I)

The present application is further directed toward a plurality of processes for preparing these compounds and their use for controlling unwanted microorganisms, and also novel intermediates and their preparation.

11 Claims, No Drawings

CARBOXAMIDES FOR CONTROLLING MICRO-ORGANISMS IN PLANT AND MATERIAL PROTECTION

CROSS REFERENCE TO RELATED APPLICATIONS

This is a §371 National Stage Application of International Application No. PCT/EP2006/011653, filed Dec. 5, 2006, which claims priority to German Application No. 10 2005 060 466.8, filed Dec. 17, 2005, which is incorporated herein by reference.

BACKGROUND OF THE INVENTION

1. Field of the Invention

The present invention relates to novel carboxamides, to a plurality of processes for their preparation and to the use for controlling harmful microorganisms in crop protection and in the protection of materials.

2. Description of Related Art

It is already known that numerous carboxamides have fungicidal properties (cf., for example, WO 03/070705, EP-A 0 545 099 and JP-A 9-132567). The activity of the compounds described in these publications is good; however, at low application rates it is sometimes unsatisfactory.

SUMMARY OF THE INVENTION

This invention now provides novel carboxamides of the formula (I)

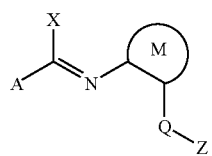

(I)

in which

X represents $OR^1$, $SR^2$, $NHR^3$, $NR^4R^5$, $SOR^6$, $SO_2R^6$, $R^1$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl, $R^2$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), —$CH_2S$—CN, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl, $R^3$, $R^4$ and $R^5$ independently of one another represent amino, hydroxyl, cyano, $C_1$-$C_{12}$-alkyl, $C_1$-$C_8$-alkoxy, $C_2$-$C_8$-alkenyl, $C_2$-$C_8$-alkynyl, $C_1$-$C_6$-alkylamino, di($C_1$-$C_6$-alkyl)amino, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), phenoxy, phenylamino, benzyloxy or benzylamino, $R^6$ represents $C_1$-$C_{12}$-alkyl or $C_1$-$C_8$-haloalkyl, M represents a phenyl, thiophene, pyridine, pyrimidine, pyridazine or pyrazine ring, each of which is monosubstituted by $R^7$, or represents a thiazole ring which is substituted by $R^8$, $R^7$ represents hydrogen, fluorine, chlorine, methyl, isopropyl, methylthio or trifluoromethyl, $R^8$ represents hydrogen, methyl, methylthio or trifluoromethyl, Q represents a direct bond, $C_1$-$C_4$-alkylene, $C_2$-$C_4$-alkenylene, O, S, SO, $SO_2$ or $NR^9$, $R^9$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl or $C_3$-$C_6$-cycloalkyl, Z represents $Z^1$, $Z^2$, $Z^3$, $Z^4$, $Z^5$ or $Z^6$, $Z^1$ represents phenyl which is optionally mono- to pentasubstituted by identical or different substituents, $Z^2$ represents pyridinyl which is optionally mono- to trisubstituted by identical or different substituents, $Z^3$ represents cycloalkyl or bicycloalkyl, each of which is optionally mono- or polysubstituted by identical or different halogen, alkyl and/or —$(CR^{10}R^{11})_m SiR^{12}R^{13}R^{14}$ substituents, $Z^4$ represents unsubstituted $C_2$-$C_{20}$-alkyl or represents $C_1$-$C_{20}$-alkyl which is mono- or polysubstituted by identical or different halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^{12}R^{13}R^{14}$ and/or $C_3$-$C_6$-cycloalkyl substituents, where the cycloalkyl moiety for its part may optionally be mono- or polysubstituted by identical or different halogen and/or $C_1$-$C_4$-alkyl substituents, $Z^5$ represents $C_2$-$C_{20}$-alkenyl or $C_2$-$C_{20}$-alkynyl, each of which is optionally mono- or polysubstituted by identical or different halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^{12}R^{13}R^{14}$ and/or $C_3$-$C_6$-cycloalkyl substituents, where the cycloalkyl moiety for its part may optionally be mono- or polysubstituted by identical or different halogen and/or $C_1$-$C_4$-alkyl substituents, $Z^6$ represents an optionally mono- or polysubstituted saturated or unsaturated 3- to 7-membered ring which contains a silicon atom as ring member, in which case Q represents a direct bond or $C_1$-$C_4$-alkylene, $R^{10}$ represents hydrogen or $C_1$-$C_4$-alkyl, $R^{11}$ represents hydrogen or $C_1$-$C_4$-alkyl, m represents 0, 1, 2 or 3, $R^{12}$ and $R^{13}$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, $R^{14}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl, or M-Q-Z together represent 1H-2,3-dihydroinden-4-yl, 1,3-dihydro-2-benzofuran-4-yl or 1,3-dihydro-2-benzothien-4-yl, each of which is optionally mono- to trisubstituted by methyl, A represents one of the radicals A1 to A19 below

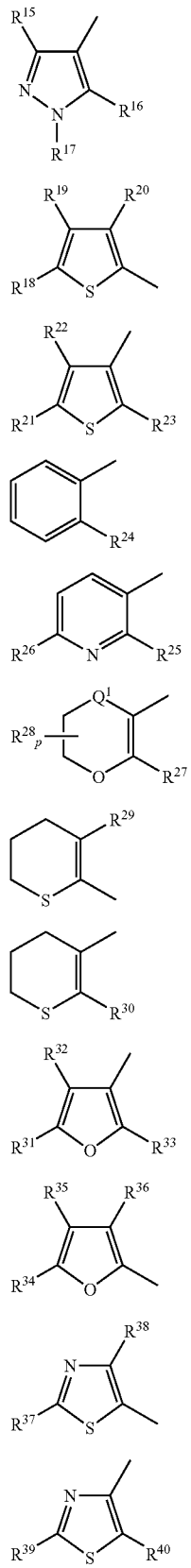
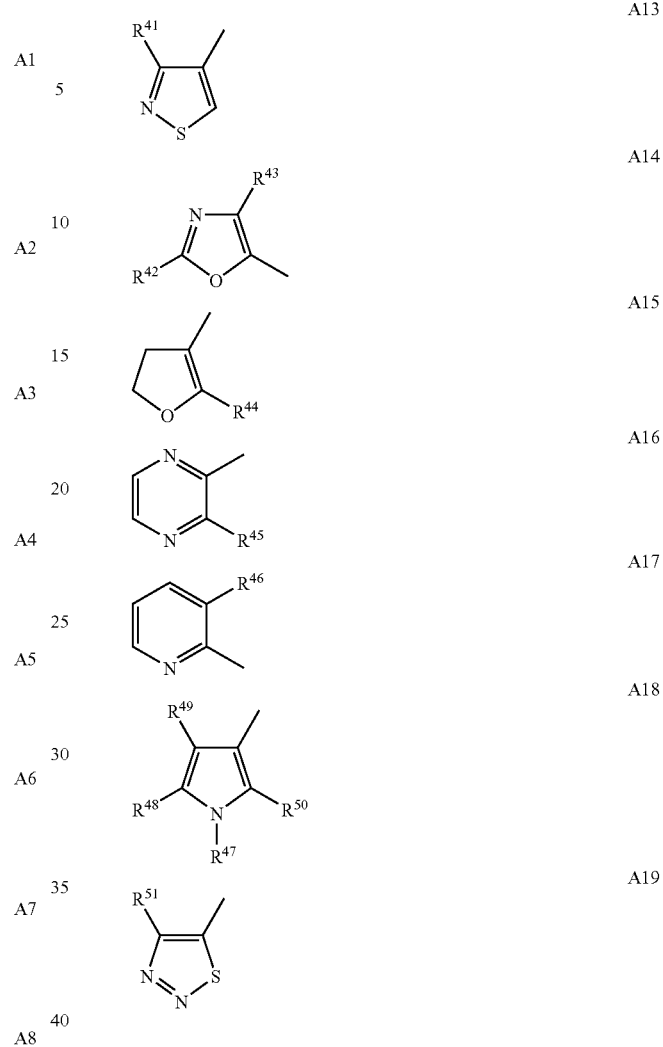

R¹⁵ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, R¹⁶ represents hydrogen, halogen, cyano, $C_1$-$C_4$-alkyl, $C_1$-$C_4$-alkoxy or $C_1$-$C_4$-alkylthio, R¹⁷ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, R¹⁸ and R¹⁹ independently of one another, represent hydrogen, halogen, $C_1$-$C_4$-alkyl or $C_1$-$C_4$-haloalkyl having 1 to 5 halogen atoms, R²⁰ represents halogen, cyano or $C_1$-$C_4$-alkyl, or $C_1$-$C_4$-haloalkyl or $C_1$-$C_4$-haloalkoxy having in each case 1 to 5 halogen atoms, R²¹ and R²² independently of one another represent hydrogen, halogen, $C_1$-$C_4$-alkyl or $C_1$-$C_4$-haloalkyl having 1 to 5 halogen atoms, R²³ represents hydrogen, halogen, $C_1$-$C_4$-alkyl or $C_1$-$C_4$-haloalkyl having 1 to 5 halogen atoms, R²⁴ represents hydrogen, halogen, hydroxy, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, $R^{25}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{26}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, $R^{27}$ represents $C_1$-$C_4$-alkyl or $C_1$-$C_4$-haloalkyl having 1 to 5 halogen atoms, $R^{28}$ represents $C_1$-$C_4$-alkyl, $Q^1$ represents S (sulphur), SO, $SO_2$ or $CH_2$, p represents 0, 1 or 2, where $R^{22}$ represents identical or different radicals if p represents 2, $R^{29}$ represents $C_1$-$C_4$-alkyl or $C_1$-$C_4$-haloalkyl having 1 to 5 halogen atoms, $R^{30}$ represents $C_1$-$C_4$-alkyl or $C_1$-$C_4$-haloalkyl having 1 to 5 halogen atoms, $R^{31}$ and $R^{32}$ independently of one another represent hydrogen, halogen, amino, $C_1$-$C_4$-alkyl or $C_1$-$C_4$-haloalkyl having 1 to 5 halogen atoms, $R^{33}$ represents hydrogen, halogen, $C_1$-$C_4$-alkyl or $C_1$-$C_4$-haloalkyl having 1 to 5 halogen atoms, $R^{34}$ and $R^{35}$ independently of one another represent hydrogen, halogen, amino, nitro, $C_1$-$C_4$-alkyl or $C_1$-$C_4$-haloalkyl having 1 to 5 halogen atoms, $R^{36}$ represents hydrogen, halogen, $C_1$-$C_4$-alkyl or $C_1$-$C_4$-haloalkyl having 1 to 5 halogen atoms, $R^{37}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{38}$ represents halogen, $C_1$-$C_4$-alkyl or $C_1$-$C_4$-haloalkyl having 1 to 5 halogen atoms, $R^{39}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{40}$ represents halogen, $C_1$-$C_4$-alkyl or $C_1$-$C_4$-haloalkyl having 1 to 5 halogen atoms, $R^{41}$ represents halogen, $C_1$-$C_4$-alkyl or $C_1$-$C_4$-haloalkyl having 1 to 5 halogen atoms, $R^{42}$ represents hydrogen or $C_1$-$C_4$-alkyl, $R^{43}$ represents halogen or $C_1$-$C_4$-alkyl, $R^{44}$ represents $C_1$-$C_4$-alkyl or $C_1$-$C_4$-haloalkyl having 1 to 5 halogen atoms, $R^{45}$ represents hydrogen, halogen, $C_1$-$C_4$-alkyl or $C_1$-$C_4$-haloalkyl having 1 to 5 halogen atoms, $R^{46}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{47}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{48}$ represents hydrogen, halogen, $C_1$-$C_4$-alkyl or $C_1$-$C_4$-haloalkyl having 1 to 5 halogen atoms, $R^{49}$ represents hydrogen, halogen, cyano, $C_1$-$C_4$-alkyl or $C_1$-$C_4$-haloalkyl having 1 to 5 halogen atoms, $R^{50}$ represents hydrogen, halogen, $C_1$-$C_4$-alkyl or $C_1$-$C_4$-haloalkyl having 1 to 5 halogen atoms, $R^{51}$ represents $C_1$-$C_4$-alkyl.

DETAILED DESCRIPTION OF A PREFERRED EMBODIMENT

Furthermore, it has been found that carboxamides of the formula (I) are obtained by one of the processes described below.

(a) If X represents $OR^1$, carboxamides of the formula (II-a)

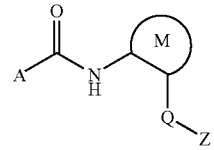

(II-a)

in which M, Q, Z and A are as defined above
are, if appropriate, in the presence of a base, reacted with an alkylating agent of the formula (III-a)

$$LG^1\text{-}R^1 \quad \text{(III-a)}$$

in which
$R^1$ is as defined above and
$LG^1$ represents a leaving group
or with a Meerwein salt of the formula (III-d)

$$(R^1)_3O^+E^- \quad \text{(III-d)}$$

in which
$R^1$ is as defined above and
E represents $BF_4$, $SbF_6$ or $SbCl_6$,
giving carboxamides of the formula (I-a)

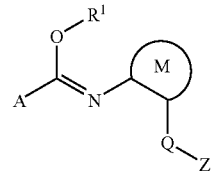

(I-a)

in which $R^1$, M, Q, Z and A are as defined above.

(b) If X represents $SR^2$, $SOR^6$ or $SO_2R^6$, in a first step carboxamides of the formula (II-a)

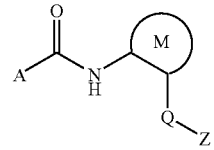

(II-a)

in which M, Q, Z and A are as defined above
are, if appropriate in the presence of a diluent, reacted with a thionating agent,
thus giving carboxamides of the formula (II-b)

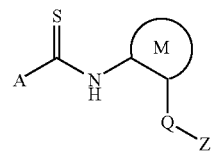

(II-b)

in which M, Q, Z and A are as defined above
which, in a second step, are, if appropriate in the presence of a base, reacted with an alkylating agent of the formula (III-b) or the formula (III-c)

$$LG^2\text{-}R^2 \quad \text{(III-b)}$$

$$LG^6\text{-}R^6 \quad \text{(III-c)}$$

in which
R$^2$ and R$^6$ are as defined above,
LG$^2$ represents a leaving group,
LG$^6$ represents a leaving group,
giving carboxamides of the formula (I-b) or the formula (I-c)

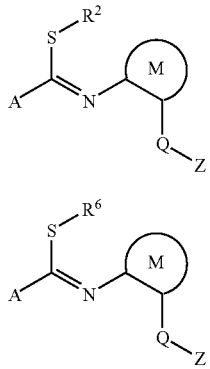

(I-b)

(I-c)

in which R$^2$, R$^6$, M, Q, Z and A are as defined above,
and, in a third step, the carboxamides of the formula (I-c) are then reacted with an oxidizing agent, if appropriate in the presence of a diluent, if appropriate in the presence of an acid binder and if appropriate in the presence of a catalyst, thus giving the carboxamides of the formula (I-d)

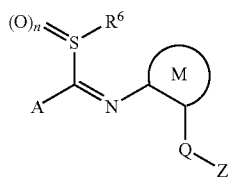

(I-d)

in which
R$^6$, M, Q, Z and A are as defined above and
n represents 1 or 2.
(c) If X represents NHR$^3$ or NR$^4$R$^5$, carboxamides of the formula (II-b)

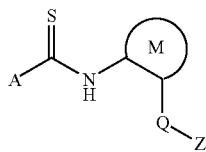

(II-b)

in which M, Q, Z and A are as defined above
are, if appropriate in the presence of a base, reacted with an amidating agent of the formula (IV-a) or the formula (IV-b)

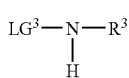

(IV-a)

-continued

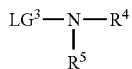

(IV-b)

in which
R$^3$, R$^4$ and R$^5$ are as defined above and
LG$^3$ represents a leaving group,
giving carboxamides of the formula (I-e) or the formula (I-f)

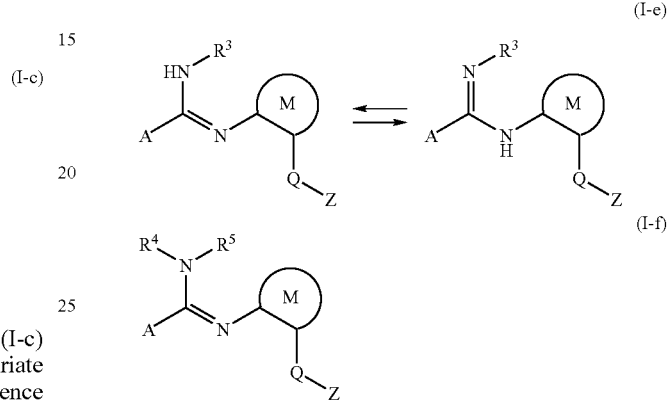

(I-e)

(I-f)

in which R$^3$, R$^4$, R$^5$, M, Q, Z and A are as defined above.
Finally, it has been found that the novel carboxamides of the formula (I) have very good microbicidal properties and can be used for controlling unwanted microorganisms both in crop protection and in the protection of materials.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro and the optical isomers, and the mixtures of these isomers and the possible tautomeric forms.

The formula (I) provides a general definition of the biphenylthiazolecarboxamides according to the invention. Preferred radical definitions of the formulaes mentioned above and below are stated below. These definitions apply to the end products of the formula (I) and likewise to all intermediates.
X preferably represents OR$^1$.
X also preferably represents SR$^2$.
X also preferably represents NHR$^3$ or NR$^4$R$^5$.
X also preferably represents SOR$^6$ or SO$_2$R$^6$.
R$^1$ preferably represents C$_1$-C$_8$-alkyl, C$_2$-C$_6$-alkenyl, C$_2$-C$_6$-alkynyl, C$_1$-C$_4$-haloalkyl, hydroxy-C$_1$-C$_6$-alkyl, (C$_1$-C$_2$-alkoxy)-C$_1$-C$_6$-alkyl, bis(C$_1$-C$_2$-alkoxy)-C$_1$-C$_6$-alkyl, (C$_1$-C$_2$-alkoxy)carbonyl-(C$_1$-C$_2$-alkyl); in each case optionally fluorine-, chlorine-, bromine-, C$_1$-C$_4$-alkyl- or C$_1$-C$_4$-haloalkyl-substituted benzyl, phenyl-1-ethyl, phenyl-2-ethyl, pyridinyl-(C$_1$-C$_2$-alkyl) or thienyl-(C$_1$-C$_2$-alkyl); in each case optionally C$_1$-C$_4$-alkoxy, fluorine-, chlorine-, bromine-, C$_1$-C$_4$-alkyl- or C$_1$-C$_4$-haloalkyl-substituted (C$_1$-C$_4$-alkyl)carbonyl, (C$_3$-C$_6$-cycloalkyl)carbonyl, phenylcarbonyl, pyridinylcarbonyl or thienylcarbonyl.
R$^1$ particularly preferably represents methyl, ethyl, n-, isopropyl, n, i-, s-, t-butyl, allyl, propargyl, trifluoromethyl, difluoromethyl, trichloromethyl, dichloromethyl, —CH₂CF₃, pentafluoroethyl, hydroxymethyl, hydroxyethyl, hydroxypropyl, methoxymethyl, methoxyethyl, ethoxymethyl, ethoxyethyl, dimethoxymethyl, dimethoxyethyl, diethoxymethyl, diethoxyethyl, methoxycarbonylmethyl, methoxycarbonylethyl, ethoxycarbonylmethyl, ethoxycarbonylethyl; in each case optionally fluorine-, chlorine-, bromine-, methyl- or trifluoromethyl-substituted benzyl, phenyl-1-ethyl, phenyl-2-ethyl, pyridinyl-(C₁-C₂-alkyl) or thienyl-(C₁-C₂-alkyl); in each case optionally methoxy-, ethoxy-, fluorine-, chlorine-, bromine-, methyl-, trifluoromethyl-substituted methylcarbonyl, ethylcarbonyl, cyclopropylcarbonyl, cyclohexylcarbonyl, phenylcarbonyl, pyridinylcarbonyl or thienylcarbonyl.

R¹ very particularly preferably represents methyl, ethyl, n-propyl, n-butyl, n-hexyl, n-octyl, n-decyl, n-dodecyl, allyl, propargyl, trifluoromethyl, trichloromethyl, —CH₂CF₃, pentafluoroethyl, hydroxymethyl, hydroxyethyl, hydroxypropyl, methoxymethyl, methoxyethyl, ethoxymethyl, ethoxyethyl, dimethoxymethyl, dimethoxyethyl, diethoxymethyl, diethoxyethyl, methoxy-carbonylmethyl, methoxycarbonylethyl, ethoxycarbonylmethyl, ethoxycarbonylethyl; in each case optionally fluorine-, chlorine-, bromine-, methyl- or trifluoromethyl-substituted benzyl, phenyl-1-ethyl, phenyl-2-ethyl, pyridinyl-(C₁-C₂-alkyl) or thienyl-(C₁-C₂-alkyl) (with emphasis 6-chloro-3-pyridinylmethyl, 2,6-dichloro-4-pyridinylmethyl, 4,5-dibromo-2-thienyl); in each case optionally methoxy-, ethoxy-, fluorine-, chlorine-, bromine-, methyl-, trifluoromethyl-substituted methylcarbonyl, ethylcarbonyl, cyclopropylcarbonyl, cyclohexylcarbonyl, phenylcarbonyl, pyridinylcarbonyl or thienylcarbonyl (with emphasis 6-chloro-3-pyridinylcarbonyl, 2,6-dichloro-4-pyridinylcarbonyl, 4,5-dibromo-2-thienylcarbonyl).

R² preferably represents C₁-C₈-alkyl, dodecyl, C₂-C₆-alkenyl, C₂-C₆-alkynyl, C₁-C₄-haloalkyl, hydroxy-C₁-C₆-alkyl, (C₁-C₂-alkoxy)-C₁-C₆-alkyl, bis(C₁-C₂-alkoxy)-C₁-C₆-alkyl, cyano-(C₁-C₄-alkyl), —CH₂S—CN, (C₁-C₂-alkoxy)carbonyl-(C₁-C₂-alkyl); in each case optionally fluorine-, chlorine-, bromine-, C₁-C₄-alkyl- or C₁-C₄-haloalkyl-substituted benzyl, phenyl-1-ethyl, phenyl-2-ethyl, pyridinyl-(C₁-C₂-alkyl) or thienyl-(C₁-C₂-alkyl); in each case optionally C₁-C₄-alkoxy-, fluorine-, chlorine-, bromine-, C₁-C₄-alkyl- or C₁-C₄-haloalkyl-substituted (C₁-C₄-alkyl)carbonyl, (C₃-C₆-cycloalkyl)carbonyl, phenylcarbonyl, pyridinylcarbonyl or thienylcarbonyl.

R² particularly preferably represents methyl, ethyl, n-, isopropyl, n-, i-, s-, t-butyl, n-hexyl, n-octyl, n-decyl, dodecyl, allyl, propargyl, trifluoromethyl, difluoromethyl, trichloromethyl, dichloromethyl, —CH₂CF₃, pentafluoroethyl, hydroxymethyl, hydroxyethyl, hydroxypropyl, methoxymethyl, methoxyethyl, ethoxymethyl, ethoxyethyl, dimethoxymethyl, dimethoxyethyl, diethoxymethyl, diethoxyethyl, cyanomethyl, cyanoethyl, —CH₂S—CN, methoxycarbonylmethyl, methoxycarbonylethyl, ethoxycarbonylmethyl, ethoxycarbonylethyl; in each case optionally fluorine-, chlorine-, bromine-, methyl- or trifluoromethyl-substituted benzyl, phenyl-1-ethyl, phenyl-2-ethyl, pyridinyl-(C₁-C₂-alkyl) or thienyl-(C₁-C₂-alkyl); in each case optionally methoxy-, ethoxy-, fluorine-, chlorine-, bromine-, methyl-, trifluoromethyl-substituted methylcarbonyl, ethylcarbonyl, cyclopropylcarbonyl, cyclohexylcarbonyl, phenylcarbonyl, pyridinylcarbonyl or thienylcarbonyl.

R² very particularly preferably represents methyl, ethyl, n-propyl, n-butyl, n-hexyl, n-octyl, n-decyl, n-dodecyl, allyl, propargyl, trifluoromethyl, trichloromethyl, —CH₂CF₃, penta-fluoroethyl, hydroxymethyl, hydroxyethyl, hydroxypropyl, methoxymethyl, methoxyethyl, ethoxymethyl, ethoxyethyl, dimethoxymethyl, dimethoxyethyl, diethoxymethyl, diethoxyethyl, cyanomethyl, cyanoethyl, —CH₂S—CN, methoxycarbonylmethyl, methoxy-carbonylethyl, ethoxycarbonylmethyl, ethoxycarbonylethyl; in each case optionally fluorine-, chlorine-, bromine-, methyl- or trifluoromethyl-substituted benzyl, phenyl-1-ethyl, phenyl-2-ethyl, pyridinyl-(C₁-C₂-alkyl) or thienyl-(C₁-C₂-alkyl) (with emphasis 6-chloro-3-pyridinylmethyl, 2,6-dichloro-4-pyridinylmethyl, 4,5-dibromo-2-thienyl); in each case optionally methoxy-, ethoxy-, fluorine-, chlorine-, bromine-, methyl-, trifluoromethyl-substituted methylcarbonyl, ethylcarbonyl, cyclopropylcarbonyl, cyclohexylcarbonyl, phenylcarbonyl, pyridinylcarbonyl or thienylcarbonyl (with emphasis 6-chloro-3-pyridinylcarbonyl, 2,6-dichloro-4-pyridinylcarbonyl, 4,5-dibromo-2-thienylcarbonyl).

R³, R⁴ and R⁵ independently of one another preferably represent hydrogen, amino, hydroxyl, cyano, C₁-C₈-alkyl, C₁-C₆-alkoxy, C₂-C₆-alkenyl, C₂-C₆-alkynyl, C₁-C₄-alkylamino, di(C₁-C₄-alkyl)amino, hydroxy-C₁-C₆-alkyl, (C₁-C₂-alkoxy)-C₁-C₆-alkyl, bis(C₁-C₂-alkoxy)-C₁-C₆-alkyl, cyano-(C₁-C₄-alkyl), phenoxy, phenylamino, benzyloxy or benzylamino.

R³, R⁴ and R⁵ independently of one another particularly preferably represent hydrogen, amino, hydroxyl, cyano, methyl, ethyl, n-, isopropyl, n-, i-, s-, t-butyl, methoxy, ethoxy, n-, isopropoxy, n-, i-, s-, t-butoxy, allyl, propargyl, methylamino, ethylamino, n-, isopropylamino, n-, i-, s-, t-butylamino, dimethylamino, diethylamino, hydroxymethyl, hydroxyethyl, hydroxypropyl, methoxymethyl, methoxyethyl, ethoxymethyl, ethoxyethyl, dimethoxymethyl, dimethoxyethyl, diethoxymethyl, diethoxyethyl, cyanomethyl, phenoxy, phenylamino, benzyloxy or benzylamino.

R⁶ preferably represents C₁-C₄-alkyl or C₁-C₄-haloalkyl.

R⁶ particularly preferably represents methyl, ethyl, n-, isopropyl, n-, i-, s-, t-butyl, trifluoro-methyl, difluoromethyl, trichloromethyl, dichloromethyl, —CH₂CF₃, pentafluoroethyl.

R⁶ very particularly preferably represents methyl, ethyl, trifluoromethyl, trichloromethyl, —CH₂CF₃, pentafluoroethyl.

M preferably represents one of the cycles below

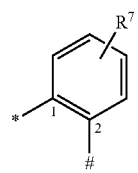

M-1

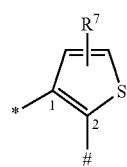

M-2

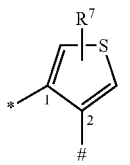
M-3

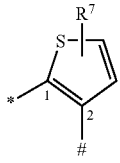
M-4

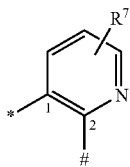
M-5

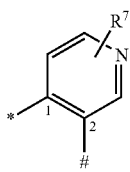
M-6

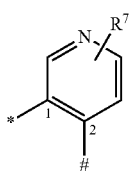
M-7

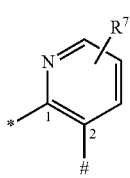
M-8

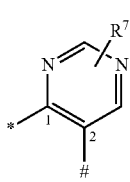
M-9

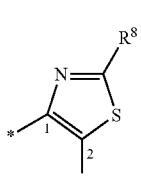
M-10

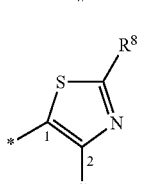
M-11

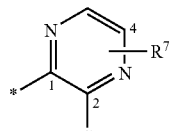
M-12

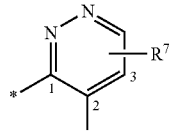
M-13

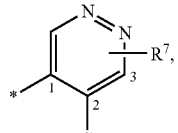
M-14 where the bond marked "*" is linked to the amide and the bond marked "#" is linked to the radical R.

M particularly preferably represents a cycle selected from the group consisting of M-1, M-2, M-3, M-4, M-5, M-6, M-9, M-10 and M-11.

M very particularly preferably represents a cycle selected from the group consisting of M-1, M-2, M-5, M-6, M-9, M-10 and M-11.

M especially preferably represents the cycle M-1.

M furthermore especially preferably represents the heterocycle M-2.

M furthermore especially preferably represents the heterocycle M-5.

M furthermore especially preferably represents the heterocycle M-6.

M furthermore especially preferably represents the heterocycle M-9.

M furthermore especially preferably represents the heterocycle M-10.

M furthermore especially preferably represents the heterocycle M-11.

$R^7$ preferably represents hydrogen.

$R^7$ furthermore, if M represents M-1, preferably represents fluorine, where fluorine is particularly preferably located in the 4-, 5- or 6-position, very particularly preferably in the 4- or 6-position, especially in the 4-position, of the anilide radical.

$R^7$ furthermore, if M represents M-1, preferably represents chlorine, where chlorine is particularly preferably located in the 5-position of the anilide radical.

$R^7$ furthermore, if M represents M-1, preferably represents methyl, where methyl is particularly preferably located in the 3-position of the anilide radical.

$R^7$ furthermore, if M represents M-1, preferably represents trifluoromethyl, where trifluoromethyl is particularly preferably located in the 4- or 5-position of the anilide radical.

$R^7$ furthermore, if M represents M-2, M-3 or M-4, preferably represents chlorine, where chlorine is particularly preferably located in the 5-position (M-2, M-3) or in the 3-position (M-4).

$R^7$ furthermore, if M represents M-2, M-3 or M-4, preferably represents methyl, where methyl is particularly preferably located in the 5-position (M-2, M-3) or in the 3-position (M-4).

$R^7$ furthermore, if M represents M-5, M-6, M-7 or M-8, preferably represents fluorine, where fluorine is particularly preferably located in the 6-position (M-5, M-6) or in the 3-position (M-7, M-8).

$R^7$ furthermore, if M represents M-5, M-6, M-7 or M-8, preferably represents chlorine, where chlorine is particularly preferably located in the 6-position (M-5, M-6) or in the 3-position (M-7, M-8).

$R^7$ furthermore, if M represents M-5, M-6, M-7 or M-8, preferably represents methyl, where methyl is particularly preferably located in the 4-position (M-5) or in the 3-position (M-6, M-7, M-8).

$R^7$ furthermore, if M represents M-9, preferably represents methyl, where methyl is particularly preferably located in the 3-position.

$R^7$ furthermore, if M represents M-9, preferably represents trifluoromethyl, where trifluoromethyl is particularly preferable located in the 3-position.

$R^7$ furthermore, if M represents M-12, preferably represents methyl, where methyl is particularly preferably located in the 4-position.

$R^7$ furthermore, if M represents M-12, preferably represents trifluoromethyl, where trifluoromethyl is particularly preferably located in the 4-position.

$R^7$ furthermore, if M represents M-13, preferably represents methyl, where methyl is particularly preferably located in the 3-position.

$R^7$ furthermore, if M represents M-13, preferably represents trifluoromethyl, where trifluoromethyl is particularly preferably located in the 3-position.

$R^7$ furthermore, if M represents M-14, preferably represents methyl, where methyl is particularly preferably located in the 3-position.

$R^7$ furthermore, if M represents M-14, preferably represents trifluoromethyl, where trifluoromethyl is particularly preferably located in the 3-position.

$R^8$ preferably represents hydrogen.

$R^8$ furthermore preferably represents methyl.

$R^8$ furthermore preferably represents trifluoromethyl.

Q preferably represents a direct bond.

Q furthermore preferably represents —$CH_2$—, —$(CH_2)_2$—, —$(CH_2)_3$—, —$CH(CH_3)$—, —$C(CH_3)_2$—, particularly preferably represents —$CH_2$—, —$(CH_2)_2$—, —$CH(CH_3)$—.

Q furthermore preferably represents —CH=CH—, —$CH_2$—CH=CH—, —$CH(CH_3)$—CH=CH—, particularly preferably represents —CH=CH—, —$CH_2$—CH=CH—.

Q furthermore preferably represents O.

Q furthermore preferably represents S.

Q furthermore preferably represents SO.

Q furthermore preferably represents $SO_2$.

Q furthermore preferably represents $NR^9$, particularly preferably NH.

$R^9$ preferably represents hydrogen, $C_1$-$C_6$-alkyl, $C_1$-$C_3$-alkoxy-$C_1$-$C_3$-alkyl, $C_1$-$C_3$-alkylthio-$C_1$-$C_3$-alkyl or $C_3$-$C_6$-cycloalkyl.

$R^9$ particularly preferably represents hydrogen, methyl, ethyl, n- or isopropyl, n-, sec-, iso- or tert-butyl, methoxymethyl, ethoxymethyl, methoxyethyl, ethoxyethyl, methylthiomethyl, ethylthiomethyl, methylthioethyl, ethylthioethyl or cyclopropyl.

$R^9$ very particularly preferably represents hydrogen, methyl, ethyl, n- or isopropyl, iso- or tert-butyl, methoxymethyl or methylthiomethyl.

Z preferably represents $Z^1$.

$Z^1$ preferably represents phenyl which is optionally mono- to pentasubstituted by identical or different substituents, where the substituents are in each case selected from the list $W^1$.

$Z^1$ particularly preferably represents monosubstituted phenyl, where the substituents are selected from the list $W^1$.

$Z^1$ also particularly preferably represents phenyl which is disubstituted by identical or different substituents, where the substituents are selected from the list $W^1$.

$Z^1$ also particularly preferably represents phenyl which is trisubstituted by identical or different substituents, where the substituents are selected from the list $W^1$.

$Z^1$ very particularly preferably represents phenyl which is monosubstituted in the 4-position, where the substituents are selected from the list $W^1$.

$Z^1$ very particularly preferably represents phenyl which is disubstituted by identical or different substituents in the 3,4-position, where the substituents are selected from the list $W^1$.

$Z^1$ very particularly preferably represents phenyl which is disubstituted by identical or different substituents in the 2,3-position, where the substituents are selected from the list $W^1$.

$Z^1$ very particularly preferably represents phenyl which is disubstituted by identical or different substituents in the 2,4-position, where the substituents are selected from the list $W^1$.

$Z^1$ very particularly preferably represents phenyl which is disubstituted by identical or different substituents in the 3,5-position, where the substituents are selected from the list $W^1$.

$Z^1$ very particularly preferably represents phenyl which is trisubstituted by identical or different substituents in the 2,4,6-position, where the substituents are selected from the list $W^1$.

$W^1$ represents halogen, cyano, nitro, amino, hydroxyl, formyl, carboxy, carbamoyl, thio-carbamoyl;

in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkyl-sulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkyl-carbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkynylcarbonyl having 2 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;

or the groupings —(CR$^{10}$R$^{11}$)$_m$SiR$^{12}$R$^{13}$R$^{14}$ or —C(Q$^2$)=N-Q$^3$, in which
- Q$^2$ represents hydrogen, hydroxyl or alkyl having 1 to 4 carbon atoms, haloalkyl having 1 to 4 carbon atoms and 1 to 9 fluorine, chlorine and/or bromine atoms or cycloalkyl having 1 to 6 carbon atoms and
- Q$^3$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkynyloxy having in each case 2 to 4 carbon atoms,
- and also phenyl, phenoxy, phenylthio, benzoyl, benzoylethenyl, cinnamoyl, heterocyclyl or phenylalkyl, phenylalkyloxy, phenylalkylthio or heterocyclylalkyl having in each case 1 to 3 carbon atoms in the respective alkyl moieties, each of which radicals is optionally mono- to trisubstituted in the ring moiety by halogen and/or straight-chain or branched alkyl or alkoxy having 1 to 4 carbon atoms.

W$^1$ preferably represents fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy, or the groupings —CH$_2$Si(CH$_3$)$_3$, —Si(CH$_3$)$_3$ or —C(Q$^2$)=N-Q$^3$, in which
- Q$^2$ represents hydrogen, methyl, ethyl or trifluoromethyl and
- Q$^3$ represents hydroxyl, methoxy, ethoxy, propoxy or isopropoxy.

Z preferably represents Z$^2$.

Z$^2$ preferably represents 2-pyridinyl, 3-pyridinyl or 4-pyridinyl, each of which is optionally mono- to trisubstituted by identical or different substituents, where the substituents are in each case selected from the list W$^2$.

Z$^2$ particularly preferably represents in each case monosubstituted 2-pyridinyl, 3-pyridinyl or 4-pyridinyl, where the substituents are in each case selected from the list W$^2$.

Z$^2$ also particularly preferably represents 2-pyridinyl, 3-pyridinyl or 4-pyridinyl, each of which is disubstituted by identical or different substituents, where the substituents are in each case selected from the list W$^2$.

Z$^2$ also particularly preferably represents 2-pyridinyl, 3-pyridinyl or 4-pyridinyl, each of which is trisubstituted by identical or different substituents, where the substituents are in each case selected from the list W$^2$.

Z$^2$ very particularly preferably represents 2-pyridinyl which is monosubstituted in the 5-position or 3-pyridinyl which is monosubstituted in the 6-position, where the substituents are in each case selected from the list W$^2$.

Z$^2$ very particularly preferably represents 2-pyridinyl which is disubstituted by identical or different substituents in the 3,5-position, where the substituents are selected from the list W$^2$.

Z$^2$ very particularly preferably represents 3-pyridinyl which is disubstituted by identical or different substituents in the 4,6-position, where the substituents are selected from the list W$^2$.

Z$^2$ very particularly preferably represents 4-pyridinyl which is disubstituted by identical or different substituents in the 3,5-position, where the substituents are selected from the list W$^2$.

W$^2$ represents hydrogen, halogen, cyano, nitro, C$_1$-C$_6$-alkyl, C$_2$-C$_4$-alkenyl, C$_2$-C$_4$-alkynyl, C$_1$-C$_4$-alkoxy, C$_1$-C$_4$-alkylthio, C$_1$-C$_4$-alkylsulphinyl, C$_1$-C$_4$-alkylsulphonyl, C$_3$-C$_6$-cycloalkyl; represents C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 5 halogen atoms; represents —SO$_2$NR$^{52}$R$^{53}$, —C(=X)R$^{54}$, —Si(R$^{55}$)$_3$, C$_2$-C$_4$-alkenylene-Si(R$^{55}$)$_3$, C$_2$-C$_4$-alkynylene-Si(R$^{55}$)$_3$, —NR$^{52}$R$^{53}$, —CH$_2$—NR$^{52}$R$^{53}$, in which
- R$^{52}$ represents hydrogen, C$_1$-C$_4$-alkyl or —C(=X)R$^{54}$,
- R$^{53}$ represents hydrogen, C$_1$-C$_4$-alkyl or —C(=X)R$^{54}$,
- R$^{52}$ and R$^{53}$ furthermore together with the nitrogen atom to which they are attached form a saturated heterocycle which has 5 to 8 ring atoms and is optionally mono- or polysubstituted by identical or different substituents from the group consisting of halogen and C$_1$-C$_4$-alkyl, where the heterocycle may contain 1 or 2 further non-adjacent heteroatoms from the group consisting of oxygen, sulphur and NR$^{56}$,
- R$^{54}$ represents hydrogen, C$_1$-C$_4$-alkyl, C$_1$-C$_4$-alkoxy or —NR$^{57}$R$^{58}$,
- R$^{55}$ represents hydrogen, C$_1$-C$_8$-alkyl, C$_1$-C$_8$-alkoxy, C$_1$-C$_4$-alkoxy-C$_1$-C$_4$-alkyl, C$_1$-C$_4$-alkylthio-C$_1$-C$_4$-alkyl or C$_1$-C$_6$-haloalkyl, where the three radicals R$^{55}$ may in each case be identical or different,
- R$^{56}$ represents hydrogen or C$_1$-C$_6$-alkyl,
- R$^{57}$ represents hydrogen or C$_1$-C$_4$-alkyl,
- R$^{58}$ represents hydrogen or C$_1$-C$_4$-alkyl,
- R$^{57}$ and R$^{58}$ furthermore together with the nitrogen atom to which they are attached represent a saturated heterocycle having 5 to 8 ring atoms which is optionally mono- or polysubstituted by identical or different substituents from the group consisting of halogen and C$_1$-C$_4$-alkyl, where the heterocycle may contain 1 or 2 further non-adjacent heteroatoms from the group consisting of oxygen, sulphur and NR$^{56}$, W$^2$ preferably represents hydrogen, fluorine, chlorine, bromine, cyano, nitro, methyl, ethyl, n- or isopropyl, n-, iso-, sec- or tert-butyl, allyl, propargyl, methoxy, ethoxy, n- or isopropoxy, n-, iso-, sec- or tert-butoxy, methylthio, ethylthio, n- or isopropylthio, n-, iso-, sec- or tert-butylthio, methylsulphinyl, ethylsulphinyl, n- or isopropylsulphinyl, n-, iso-, sec- or tert-butylsulphinyl, methylsulphonyl, ethylsulphonyl, n- or iso-propylsulphonyl, n-, iso-, sec- or tert-butylsulphonyl, cyclopropyl, cyclopentyl, cyclohexyl, trifluoromethyl, difluoromethyl, trichloromethyl, trifluoroethyl, trifluoromethoxy, difluoromethoxy, trichloromethoxy, difluoromethylthio, difluorochloromethylthio, trifluoromethylthio, trifluoromethylsulphinyl, trifluoromethylsulphonyl, —SO$_2$NMe$_2$, —C(=X)R$^{54}$, —Si(R$^{55}$)$_3$, —CH=CH—Si(R$^{55}$)$_3$, —CH$_2$—CH=CH—Si(R$^{55}$)$_3$, —CH=CH—CH$_2$—Si(R$^{55}$)$_3$, —C≡C—Si(R$^{55}$)$_3$, —CH$_2$—C≡C—Si(R$^{55}$)$_3$, —C≡C—CH$_2$—Si(R$^{55}$)$_3$, —CH$_2$—C≡C—CH$_2$—Si(R$^{55}$)$_3$, —NR$^{52}$R$^{53}$, —CH$_2$—NR$^{52}$R$^{53}$.

R$^{52}$ preferably represents hydrogen, methyl, ethyl, n- or isopropyl or —C(=X)R$^{54}$.

R$^{52}$ particularly preferably represents hydrogen or methyl.

R$^{53}$ preferably represents hydrogen, methyl, ethyl, n- or isopropyl or —C(=X)R$^{54}$.

R$^{53}$ particularly preferably represents hydrogen or methyl.

R$^{52}$ and R$^{53}$ furthermore together with the nitrogen atom to which they are attached preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by R$^{56}$.

$R^{54}$ preferably represents hydrogen, methyl, ethyl, n- or isopropyl, methoxy, ethoxy, n- or isopropoxy or —$NR^{57}R^{58}$ $R^{54}$ particularly preferably represents hydrogen, methyl, ethyl, methoxy, ethoxy or —$NR^{57}R^{58}$.

$R^{55}$ preferably represents methyl, ethyl, methoxy, ethoxy, methoxymethyl, ethoxymethyl, methoxyethyl, ethoxyethyl, methylthiomethyl, ethylthiomethyl, methylthioethyl or ethyl-thioethyl, where the three radicals $R^{55}$ may in each case be identical or different.

$R^{55}$ particularly preferably represents methyl, methoxy, methoxymethyl or methylthiomethyl, where the three radicals $R^{55}$ may in each case be identical or different.

$R^{55}$ very particularly preferably represents methyl.

$R^{56}$ preferably represents hydrogen or $C_1$-$C_4$-alkyl.

$R^{56}$ particularly preferably represents hydrogen, methyl, ethyl, n- or isopropyl, n-, iso-, sec- or tert-butyl.

$R^{57}$ preferably represents hydrogen, methyl, ethyl, n- or isopropyl.

$R^{57}$ particularly preferably represents hydrogen or methyl.

$R^{58}$ preferably represents hydrogen, methyl, ethyl, n- or isopropyl.

$R^{58}$ particularly preferably represents hydrogen or methyl.

$R^{57}$ and $R^{58}$ furthermore together with the nitrogen atom to which they are attached preferably form a saturated a heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^7$.

Z also preferably represents $Z^3$.

$Z^3$ preferably represents cycloalkyl or bicycloalkyl having in each case 3 to 10 carbon atoms, each of which radicals is optionally mono- to tetrasubstituted by identical or different substituents from the group consisting of halogen, $C_1$-$C_4$-alkyl, —$CH_2Si(CH_3)_3$ and/or —$Si(CH_3)_3$.

$Z^3$ particularly preferably represents cyclopropyl, cyclopentyl, cyclohexyl, cycloheptyl, cyclooctyl, cyclononyl, bicyclo[2.2.1]heptyl or bicyclo[2.2.2]octyl, each of which is optionally mono- to tetrasubstituted by identical or different substituents from the group consisting of chlorine, methyl, —$CH_2Si(CH_3)_3$ and/or —$Si(CH_3)_3$.

$Z^3$ very particularly preferably represents chlorine- and methyl-substituted cyclopropyl.

Z also preferably represents $Z^4$.

$Z^4$ preferably represents unsubstituted $C_2$-$C_{20}$-alkyl or represents $C_1$-$C_{20}$-alkyl which is mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^{12}R^{13}R^{14}$ and/or $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and/or $C_1$-$C_4$-haloalkyl.

$Z^4$ particularly preferably represents unsubstituted $C_2$-$C_{20}$-alkyl.

$Z^4$ also particularly preferably represents $C_1$-$C_{20}$-alkyl which is substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl) amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^6R^7R^8$, cyclopropyl, dichlorocyclopropyl, cyclobutyl, cyclopentyl or cyclohexyl; very particularly preferably $C_1$-$C_{20}$-alkyl which is substituted by fluorine, chlorine, methylthio, ethylthio, n- or isopropylthio, n-, iso-, sec-, tert-butylthio, pentylthio, hexylthio, methylsulphonyl, ethylsulphonyl, n- or isopropylsulphonyl, n-, iso-, sec-, tert-butylsulphonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylthio, trifluoromethoxy, —$SiR^{12}R^{13}R^{14}$, cyclopropyl, dichlorocyclopropyl, cyclobutyl, cyclopentyl or cyclohexyl.

Z also preferably represents $Z^5$.

$Z^5$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^{12}R^{13}R^{14}$ and/or $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and/or $C_1$-$C_4$-haloalkyl.

$Z^5$ particularly preferably represents $C_2$-$C_{20}$-alkenyl or $C_2$-$C_{20}$-alkynyl, each of which is optionally substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^{12}R^{13}R^{14}$, cyclopropyl, dichlorocyclopropyl, cyclobutyl, cyclopentyl or cyclohexyl.

$Z^5$ very particularly preferably represents $C_2$-$C_{20}$-alkenyl or $C_2$-$C_{20}$-alkynyl.

Z also preferably represents $Z^6$.

$Z^6$ preferably represents one of the rings below

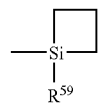

Si-1

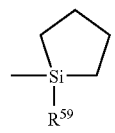

Si-2

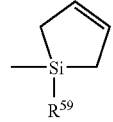

Si-3

-continued

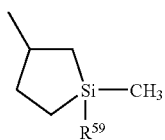
Si-4

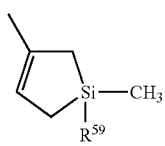
Si-5

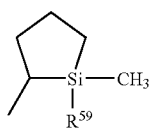
Si-6

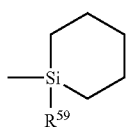
Si-7

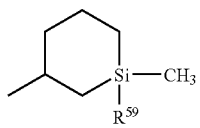
Si-8

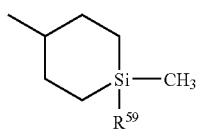
Si-9 in which $R^{59}$ represents hydrogen or methyl.

$R^{10}$ preferably represents hydrogen or methyl.

$R^{10}$ particularly preferably represents hydrogen.

$R^{11}$ preferably represents hydrogen or methyl.

$R^{11}$ particularly preferably represents hydrogen.

m preferably represents 0, 1 or 2.

$R^{12}$ and $R^{13}$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^{12}$ and $R^{13}$ independently of one another particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^{12}$ and $R^{13}$ independently of one another very particularly preferably represent methyl, methoxy, methoxymethyl or methylthiomethyl.

$R^{12}$ and $R^{13}$ especially preferably each represent methyl.

$R^{14}$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^{14}$ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^{14}$ very particularly preferably represents methyl, ethyl, n- or isopropyl, iso- or tert-butyl, methoxy, isopropoxy, iso- or tert-butoxy, methoxymethyl, methylthiomethyl or phenyl.

$R^{14}$ especially preferably represents methyl, ethyl, n- or isopropyl, iso- or tert-butyl, methoxy, isopropoxy, iso- or tert-butoxy.

$R^{14}$ most preferably represents methyl.

M-Q-Z also preferably together represents 1,1,3-trimethyl-1H-2,3-dihydroinden-4-yl, 1,3-dimethyl-1H-2,3-dihydroinden-4-yl, 1,1,3-trimethyl-1,3-dihydro-2-benzofuran-4-yl, 1,3-dimethyl-1,3-dihydro-2-benzofuran-4-yl, 1,1,3-trimethyl-1,3-dihydro-2-benzothien-4-yl or 1,3-dimethyl-1,3-dihydro-2-benzothien-4-yl.

M-Q-Z also particularly preferably together represents 1,1,3-trimethyl-1H-2,3-dihydroinden-4-yl.

A preferably represents one of the radicals A1, A2, A3, A4, A5, A6, A9, A10, A11, A12 or A17.

A particularly preferably represents one of the radicals A1, A2, A4, A5, A6, A9, A11, A16, A17.

A very particularly preferably represents the radical A1.

A furthermore very particularly preferably represents the radical A2.

A furthermore very particularly preferably represents the radical A4.

A furthermore very particularly preferably represents the radical A5.

A furthermore very particularly preferably represents the radical A6.

A furthermore very particularly preferably represents the radical A9.

A furthermore very particularly preferably represents the radical A11.

A furthermore very particularly preferably represents the radical A16.

A furthermore very particularly preferably represents the radical A17.

$R^{15}$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

$R^{15}$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^{15}$ very particularly preferably represents hydrogen, fluorine, chlorine, bromine, iodine, methyl, isopropyl, monofluoromethyl, monofluoroethyl, difluoromethyl, Trifluoromethyl, difluorochloromethyl or trichloromethyl.

$R^{15}$ especially preferably represents methyl, difluoromethyl, trifluoromethyl or 1-fluoroethyl.

$R^{16}$ preferably represents hydrogen, fluorine, chlorine, bromine, iodine, methyl, ethyl, methoxy, ethoxy, methylthio or ethylthio.

$R^{16}$ particularly preferably represents hydrogen, fluorine, chlorine, bromine, iodine or methyl.

$R^{16}$ very particularly preferably represents hydrogen, fluorine, chlorine or methyl.

$R^{17}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{17}$ particularly preferably represents hydrogen, methyl, ethyl, isopropyl, trifluoromethyl, difluoromethyl, hydroxymethyl, hydroxyethyl or phenyl.

$R^{17}$ very particularly preferably represents hydrogen, methyl, trifluoromethyl or phenyl.

$R^{17}$ especially preferably represents methyl.

$R^{18}$ and $R^{19}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{18}$ and $R^{19}$ independently of one another particularly preferably represent hydrogen, fluorine, chlorine, bromine, methyl, ethyl, difluoromethyl, trifluoromethyl, difluorochloromethyl or trichloromethyl.

$R^{18}$ and $R^{19}$ independently of one another very particularly preferably represent hydrogen, fluorine, chlorine, bromine, methyl, ethyl, difluoromethyl, trifluoromethyl or trichloromethyl.

$R^{18}$ and $R^{19}$ especially preferably each represent hydrogen.

$R^{20}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{20}$ particularly preferably represents fluorine, chlorine, bromine, cyano, methyl, trifluoromethyl, trifluoromethoxy, difluoromethoxy, difluorochloromethoxy or trichloromethoxy.

$R^{20}$ very particularly preferably represents fluorine, chlorine, bromine, iodine, methyl, trifluoromethyl or trifluoromethoxy.

$R^{20}$ especially preferably represents methyl or trifluoromethyl.

$R^{21}$ and $R^{22}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{21}$ and $R^{22}$ independently of one another particularly preferably represent hydrogen, fluorine, chlorine, bromine, methyl, ethyl, difluoromethyl, trifluoromethyl, difluorochloromethyl or trichloromethyl.

$R^{21}$ and $R^{22}$ independently of one another very particularly preferably represent hydrogen, fluorine, chlorine, bromine, methyl, ethyl, difluoromethyl, trifluoromethyl or trichloromethyl.

$R^{21}$ and $R^{22}$ especially preferably each represent hydrogen.

$R^{23}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{23}$ particularly preferably represents hydrogen, fluorine, chlorine, bromine, iodine, methyl or trifluoromethyl.

$R^{23}$ very particularly preferably represents fluorine, chlorine, bromine, iodine, methyl or trifluoromethyl.

$R^{24}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{24}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{24}$ very particularly preferably represents hydrogen, fluorine, chlorine, bromine, iodine, methyl, difluoromethyl, trifluoromethyl or trichloromethyl.

$R^{24}$ especially preferably represents iodine, methyl, difluoromethyl or trifluoromethyl.

$R^{25}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{25}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{25}$ very particularly preferably represents fluorine, chlorine, bromine, iodine, methyl, trifluoromethyl, difluoromethyl or trichloromethyl.

$R^{26}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{26}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methyl-sulphinyl or methylsulphonyl.

$R^{26}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{26}$ especially preferably represents hydrogen.

$R^{27}$ preferably represents methyl, ethyl or $C_1$-$C_2$-haloalkyl having 1 to 5 fluorine, chlorine and/or bromine atoms.

$R^{27}$ particularly preferably represents methyl, ethyl, trifluoromethyl, difluoromethyl, difluorochloromethyl or trichloromethyl.

$R^{28}$ preferably represents methyl or ethyl.

$R^{28}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{29}$ preferably represents methyl, ethyl or $C_1$-$C_2$-haloalkyl having 1 to 5 fluorine, chlorine and/or bromine atoms.

$R^{29}$ particularly preferably represents methyl, ethyl, trifluoromethyl, difluoromethyl, difluorochloromethyl or trichloromethyl.

$R^{29}$ very particularly preferably represents methyl, trifluoromethyl, difluoromethyl or trichloromethyl.

$R^{30}$ preferably represents methyl, ethyl or $C_1$-$C_2$-haloalkyl having 1 to 5 fluorine, chlorine and/or bromine atoms.

$R^{30}$ particularly preferably represents methyl, ethyl, trifluoromethyl, difluoromethyl, difluorochloromethyl or trichloromethyl.

$R^{30}$ very particularly preferably represents methyl, trifluoromethyl, difluoromethyl or trichloromethyl.

$R^{31}$ and $R^{32}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{31}$ and $R^{32}$ independently of one another particularly preferably represent hydrogen, fluorine, chlorine, bromine, methyl, ethyl, trifluoromethyl, difluoromethyl, difluorochloromethyl or trichloromethyl.

$R^{31}$ and $R^{32}$ independently of one another very particularly preferably represent hydrogen, fluorine, chlorine, bromine, methyl, trifluoromethyl, difluoromethyl or trichloromethyl.

$R^{31}$ and $R^{32}$ especially preferably refer each represent hydrogen.

$R^{33}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{33}$ particularly preferably represents hydrogen, fluorine, chlorine, bromine, iodine, methyl, ethyl, trifluoromethyl, difluoromethyl, difluorochloromethyl or trichloromethyl.

$R^{33}$ very particularly preferably represents hydrogen, fluorine, chlorine, bromine, iodine, methyl, trifluoromethyl, difluoromethyl or trichloromethyl.

$R^{33}$ especially preferably represents methyl.

$R^{34}$ and $R^{35}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine 5 atoms.

$R^{34}$ and $R^{35}$ independently of one another particularly preferably represent hydrogen, fluorine, chlorine, bromine, nitro, methyl, ethyl, trifluoromethyl, difluoromethyl, difluorochloromethyl or trichloromethyl.

$R^{34}$ and $R^{35}$ independently of one another very particularly preferably represent hydrogen, fluorine, chlorine, bromine, methyl, trifluoromethyl, difluoromethyl or trichloromethyl.

$R^{34}$ and $R^{35}$ especially preferably each represent hydrogen.

$R^{36}$ preferably represents hydrogen, fluorine, chlorine, bromine, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, methyl, ethyl, trifluoromethyl, difluoromethyl, difluorochloromethyl or trichloromethyl.

$R^{36}$ very particularly preferably represents hydrogen, fluorine, chlorine, bromine, methyl, trifluoromethyl, difluoromethyl or trichloromethyl.

$R^{36}$ especially preferably represents methyl.

$R^{37}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{37}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{37}$ very particularly preferably represents hydrogen, fluorine, chlorine, bromine, amino, methylamino, dimethylamino, methyl, trifluoromethyl, difluoromethyl or trichloromethyl.

$R^{37}$ especially preferably represents amino, methylamino, dimethylamino, methyl or trifluoromethyl.

$R^{38}$ preferably represents fluorine, chlorine, bromine, methyl, ethyl or $C_1$-$C_2$-haloalkyl having 1 to 5 fluorine, chlorine and/or bromine atoms.

$R^{38}$ particularly preferably represents fluorine, chlorine, bromine, methyl, ethyl, trifluoromethyl, difluoromethyl, difluorochloromethyl or trichloromethyl.

$R^{38}$ very particularly preferably represents fluorine, chlorine, bromine, methyl, trifluoromethyl, difluoromethyl or trichloromethyl.

$R^{38}$ especially preferably represents methyl, trifluoromethyl or difluoromethyl.

$R^{39}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{39}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{39}$ very particularly preferably represents hydrogen, fluorine, chlorine, bromine, amino, methylamino, dimethylamino, methyl, trifluoromethyl, difluoromethyl or trichloromethyl.

$R^{39}$ especially preferably represents amino, methylamino, dimethylamino, methyl or trifluoromethyl.

$R^{40}$ preferably represents fluorine, chlorine, bromine, methyl, ethyl or $C_1$-$C_2$-haloalkyl having 1 to 5 fluorine, chlorine and/or bromine atoms.

$R^{40}$ particularly preferably represents fluorine, chlorine, bromine, methyl, ethyl, trifluoromethyl, difluoromethyl, difluorochloromethyl or trichloromethyl.

$R^{40}$ very particularly preferably represents fluorine, chlorine, bromine, methyl, trifluoromethyl, difluoromethyl or trichloromethyl.

$R^{40}$ especially preferably represents methyl, trifluoromethyl or difluoromethyl.

$R^{41}$ preferably represents fluorine, chlorine, bromine, methyl, ethyl or $C_1$-$C_2$-haloalkyl having 1 to 5 fluorine, chlorine and/or bromine atoms.

$R^{41}$ particularly preferably represents fluorine, chlorine, bromine, methyl, ethyl, trifluoromethyl, difluoromethyl, difluorochloromethyl or trichloromethyl.

$R^{41}$ very particularly preferably represents fluorine, chlorine, bromine, methyl, trifluoromethyl, difluoromethyl or trichloromethyl.

$R^{42}$ preferably represents hydrogen, methyl or ethyl.

$R^{42}$ particularly preferably represents methyl.

$R^{43}$ preferably represents fluorine, chlorine, bromine, methyl or ethyl.

$R^{43}$ particularly preferably represents fluorine, chlorine or methyl.

$R^{44}$ preferably represents methyl, ethyl or $C_1$-$C_2$-haloalkyl having 1 to 5 fluorine, chlorine and/or bromine atoms.

$R^{44}$ particularly preferably represents methyl, ethyl, trifluoromethyl, difluoromethyl, difluoro-chloromethyl or trichloromethyl.

$R^{44}$ very particularly preferably represents methyl, trifluoromethyl, difluoromethyl or trichloromethyl.

$R^{44}$ especially preferably represents methyl or trifluoromethyl.

$R^{45}$ preferably represents hydrogen, fluorine, chlorine, bromine, methyl, ethyl or $C_1$-$C_2$-haloalkyl having 1 to 5 fluorine, chlorine and/or bromine atoms.

$R^{45}$ particularly preferably represents hydrogen, fluorine, chlorine, bromine, methyl or trifluoromethyl.

$R^{46}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{46}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{46}$ very particularly preferably represents fluorine, chlorine, bromine, iodine, methyl, trifluoromethyl, difluoromethyl or trichloromethyl.

$R^{47}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{47}$ particularly preferably represents hydrogen, methyl, ethyl, trifluoromethyl, methoxymethyl, ethoxymethyl, hydroxymethyl or hydroxyethyl.

$R^{47}$ very particularly preferably represents methyl or methoxymethyl.

$R^{48}$ preferably represents hydrogen, fluorine, chlorine, bromine, methyl, ethyl or $C_1$-$C_2$-haloalkyl having 1 to 5 fluorine, chlorine and/or bromine atoms.

$R^{48}$ particularly preferably represents hydrogen, fluorine, chlorine, bromine, methyl, ethyl, trifluoromethyl, difluoromethyl or trichloromethyl.

$R^{48}$ very particularly preferably represents hydrogen or methyl.

$R^{49}$ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

$R^{49}$ particularly preferably represents hydrogen, fluorine, chlorine, bromine, cyano, methyl, ethyl, isopropyl, trifluoromethyl, difluoromethyl, difluorochloromethyl or trichloromethyl.

$R^{49}$ very particularly preferably represents hydrogen, methyl, difluoromethyl or trifluoromethyl.

$R^{50}$ preferably represents hydrogen, fluorine, chlorine, bromine, methyl, ethyl or $C_1$-$C_2$-haloalkyl having 1 to 5 fluorine, chlorine and/or bromine atoms.

$R^{50}$ particularly preferably represents hydrogen, fluorine, chlorine, bromine, iodine, methyl or trifluoromethyl.

$R^{50}$ very particularly preferably represents hydrogen.

$R^{51}$ preferably represents methyl, ethyl, n-propyl or isopropyl.

$R^{51}$ particularly preferably represents methyl or ethyl.

Preference is given to those compounds of the formula (I) in which all radicals each have the meanings mentioned above as being preferred.

Particular preference is given to those compounds of the formula (I) in which all radicals each have the meanings mentioned above as being particularly preferred.

Preferred, and in each case to be understood as a sub-group of the compounds of the formula (I) mentioned above, are the following groups of novel carboxamides:

Group 1: Carboxamides of the formula (I-a)

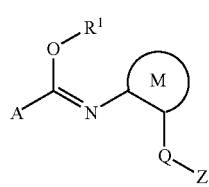

(I-a)

in which $R^1$, M, Q, Z and A are as defined above.

Group 2: Carboxamides of the formula (I-b)

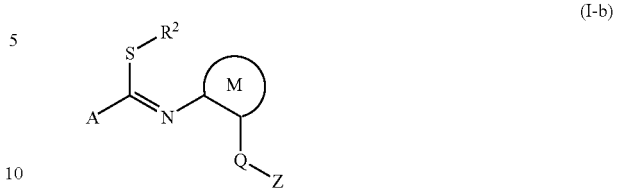

(I-b)

in which $R^2$, M, Q, Z and A are as defined above.

Group 3: Carboxamides of the formula (I-e)

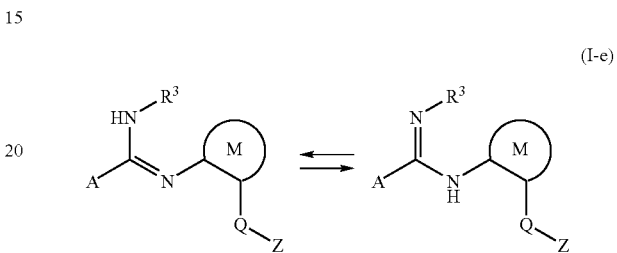

(I-e)

in which $R^3$, M, Q, Z and A are as defined above.

Group 4: Carboxamides of the formula (I-f)

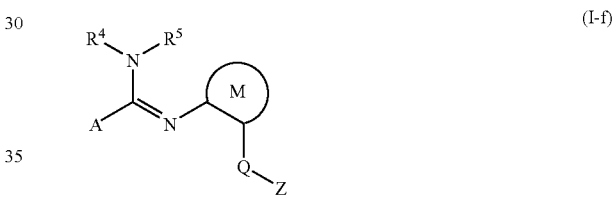

(I-f)

in which $R^4$, $R^5$, M, Q, Z and A are as defined above.

Group 5: Carboxamides of the formula (I-d)

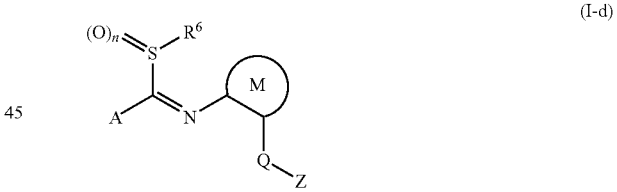

(I-d)

in which n, $R^6$, M, Q, Z and A are as defined above. n preferably represents 2.

Preference is given to carboxamides of the formula (I) and of groups 1 to 5 in which M represents M-1.
Preference is given to carboxamides of the formula (I) and of groups 1 to 5 in which M represents M-2.
Preference is given to carboxamides of the formula (I) and of groups 1 to 5 in which M represents M-5.
Preference is given to carboxamides of the formula (I) and of groups 1 to 5 in which M represents M-6.
Preference is given to carboxamides of the formula (I) and of groups 1 to 5 in which M represents M-9.
Preference is given to carboxamides of the formula (I) and of groups 1 to 5 in which M represents M-10.
Preference is given to carboxamides of the formula (I) and of groups 1 to 5 in which M represents M-11.
Preference is given to carboxamides of the formula (I) and of groups 1 to 5 in which Q represents a direct bond and Z represents $Z^1$.

Preference is given to carboxamides of the formula (I) and of groups 1 to 5 in which Q represents a direct bond and Z represents $Z^4$.

$Z^4$ especially preferably represents the grouping

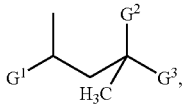

in which
$G^1$ represents hydrogen or methyl,
$G^2$ represents hydrogen or methyl,
$G^3$ represents methyl or ethyl.

$Z^4$ also preferably represents one of the groupings G1 to G8

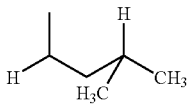 G1

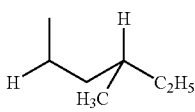 G2

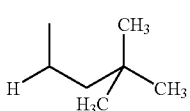 G3

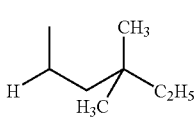 G4

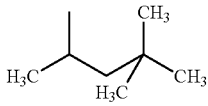 G5

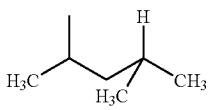 G6

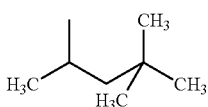 G7

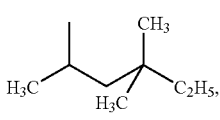 G8 particularly preferably G3, G5 or G7.

The definition $C_1$-$C_{20}$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, particularly preferably straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl is, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The substituent —$SiR^{12}R^{13}R^{14}$ preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2OCHMe_2$, $SiMe_2OCH_2CHMe_2$, $SiMe_2OMe$, $SiMe_2CMe_3$, $SiMe_2CH_2CH_2Me$.

The definition $C_2$-$C_{20}$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls, 1-methyl-1-propenyl, 1-ethyl-1-butenyl, 2,4-dimethyl-1-pentenyl, 2,4-dimethyl-2-pentenyl.

The definition $C_2$-$C_{20}$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, haloalkyl, are mono- or polyhalogenated. In the case of polyhalogenation, the halogen atoms may be identical or different. Here, halogen represents fluorine, chlorine, bromine and iodine, in particular fluorine, chlorine and bromine.

The processes according to the invention can be illustrated by the general reaction scheme below:

group, preferably halogen, triflate (trifluoromethylsulphonate), tosylate (p-toluenesulphonate), particularly preferably chlorine, bromine, iodine, triflate (trifluoromethylsulphonate), tosylate (p-toluenesulphonate).

Alkylating agents of the formula (III-a) are known.

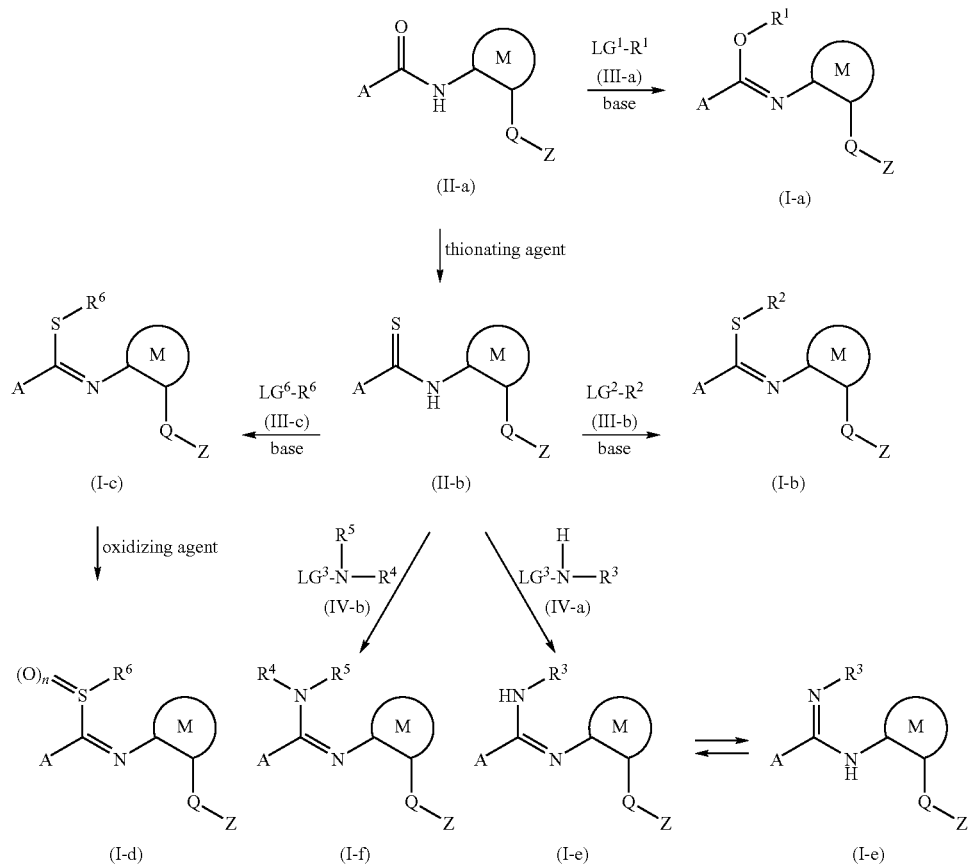

The formula (II-a) provides a general definition of the carboxamides required as starting materials for carrying out the process (a) according to the invention and also the first step of the process (b) according to the invention. In this formula (II-a), M, Q, Z and A preferably, particularly preferably, very particularly preferably and especially preferably have those meanings which have already been mentioned in connection with the description of the compounds of the formula (I) according to the invention as being preferred, particularly preferred, etc., for these radicals.

The carboxamides of the formula (II-a) are known and/or can be prepared by known processes (cf., for example, EP-A 0 545 099, WO 03/070705, WO 01/42223, JP-A 01-290662 and U.S. Pat. No. 5,093,347).

The formula (III-a) provides a general definition of the alkylating agents furthermore required as starting materials for carrying out the process (a) according to the invention. In this formula (III-a), $R^1$ preferably, particularly preferably, very particularly preferably and especially preferably has those meanings which have already been mentioned in connection with the description of the compounds of the formula (I) according to the invention as being preferred, particularly preferred, etc., for this radical. $LG^1$ represents a leaving The formula (III-d) provides a general definition of the Meerwein salts furthermore required as starting materials for carrying out the process (a) according to the invention. In this formula (III-d) $R^1$ preferably, particularly preferably, very particularly preferably and especially preferably has those meanings which have already been mentioned in connection with the description of the compounds of the formula (I) according to the invention as being preferred, particularly preferred, etc., for this radical.

Meerwein salts of the formula (III-d) are known.

The formula (II-b) provides a general definition of the carboxamides which occur as intermediates when carrying out the process (b) according to the invention or which are required as starting materials for carrying out the process (c) according to the invention. In this formula (II-b), M, Q, Z and A preferably, particularly preferably, very particularly preferably and especially preferably have those meanings which have already been mentioned in connection with the description of the compounds of the formula (I) according to the invention as being preferred, particularly preferred, etc., for these radicals.

Some of the carboxamides of the formula (II-b) are known and/or they can be prepared by known processes (cf., for example, WO 01/42223).

Novel, and thus also part of the subject-matter of the present application, are carboxamides of the formula (II-c)

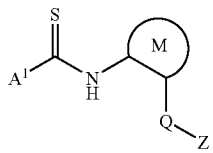

(II-c)

in which
A¹ represents A1, A2, A3, A4, A5, A6, A7, A8, A9, A10, A11, A12, A13, A14, A15, A16, A17 and A19,
M, Q and Z are as defined above,
except for compounds in which
M represents M-1,
$R^7$ represents hydrogen,
Q represents a direct bond,
Z represents phenyl which is substituted in the 4-position by halogen,
A¹ represents A1,
$R^{15}$ represents $C_1$-$C_3$-haloalkyl,
$R^{16}$ represents hydrogen,
$R^{17}$ represents $C_1$-$C_3$-alkyl, $C_1$-$C_3$-alkoxy-$C_1$-$C_3$-alkyl, $C_1$-$C_3$-haloalkyl, $C_1$-$C_3$-haloalkoxy-$C_1$-$C_3$-alkyl.

In this formula (II-c), M, Q and Z preferably, particularly preferably, very particularly preferably and especially preferably have those meanings which have already been mentioned in connection with the description of the compounds of the formula (I) according to the invention as being preferred, particularly preferred, etc., for these radicals. A¹ preferably, particularly preferably, very particularly preferably and especially preferably has those meanings which have already been mentioned in connection with the description of the compounds of the formula (I) according to the invention as being preferred, particularly preferred, etc., for the radical A. The preferred ranges apply correspondingly to the excluded compounds.

The formula (III-b) and the formula (III-c) provide general definitions of the alkylating agents furthermore required as starting materials for carrying out the process (b) according to the invention. In these formulae (III-b) and (III-c), $R^2$ and $R^6$ preferably, particularly preferably, very particularly preferably and especially preferably have those meanings which have already been mentioned in connection with the description of the compounds of the formula (I) according to the invention as being preferred, particularly preferred, etc., for these radicals. $LG^2$ represents a leaving group, preferably halogen, triflate (trifluoromethylsulphonate), tosylate (p-toluenesulphonate), particularly preferably chlorine, bromine, iodine, triflate (trifluoromethylsulphonate), tosylate (p-toluenesulphonate). $LG^6$ represents a leaving group, preferably halogen, triflate (trifluoromethylsulphonate), tosylate (p-toluenesulphonate), particularly preferably chlorine, bromine, iodine, triflate (trifluoromethylsulphonate), tosylate (p-toluenesulphonate).

Alkylating agents of the formula (III-b) and the formula (III-c) are known.

The formula (IV-a) and the formula (IV-b) provide general definitions of the amidating agents furthermore required as starting materials for carrying out the process (c) according to the invention. In these formulae (IV-a) and (IV-b) $R^3$, $R^4$ and $R^5$ preferably, particularly preferably, very particularly preferably and especially preferably have those meanings which have already been mentioned in connection with the description of the compounds of the formula (I) according to the invention as being preferred, particularly preferred, etc., for these radicals. $LG^3$ represents a leaving group, preferably hydrogen, amino, hydroxyl, trialkylsilyl, particularly preferably hydrogen, trimethylsilyl.

Amidating agents of the formula (IV-a) and the formula (IV-b) are known.

Suitable diluents for carrying out the processes (a) and (c) according to the invention and the second step of the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexanethylphosphoric triamide; mixtures thereof with water or pure water.

The processes (a) and (c) according to the invention and the second step of the process (b) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The first step of the process (b) according to the invention is carried out in the presence of a thionating agent. Suitable thionating agents are all reagents customary for such reactions. Preference is given to using sulphur, phosphorus pentasulphide ($P_2S_5$, $P_4S_{10}$) or Lawessons reagent.

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitriles; amides, such as N,N-dimethylformamide, N,N-dimethylacetamide, N-methylformanilide, N-methylpyrrolidone or hexamethylphosphoric triamide; mixtures thereof with water or pure water.

Suitable oxidizing agents for carrying out the third step of the process (b) according to the invention are all oxidizing agents customarily used for oxidizing sulphur. Particularly suitable are hydrogen peroxide, organic peracids, such as, for example, peracetic acid, m-chloroperbenzoic acid, p-nitroperbenzoic acid or atmospheric oxygen.

Suitable diluents for carrying out the third step of the process (b) according to the invention are inert organic solvents. Preference is given to using hydrocarbons, such as, benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid; or dipolar aprotic solvents, such as acetonitrile, acetone, ethyl acetate or dimethylformamide.

If appropriate, the third step of the process (b) according to the invention may be carried out in the presence of an acid binder. Suitable acid binders are all organic and inorganic acid binders customarily used. Preference is given to using alkaline earth metal or alkali metal hydroxides, acetates or carbonates, such as, for example, calcium hydroxide, sodium hydroxide, sodium acetate or sodium carbonate.

If appropriate, the third step of the process (b) according to the invention can be carried out in the presence of a suitable catalyst. Suitable catalysts are all metal salt catalysts customarily used for such sulphur oxidations. In this context, ammonium molybdate and sodium tungstate may be mentioned by way of example.

When carrying out the processes (a) and (c) according to the invention and the second step of the process (b) according to the invention, the reaction temperatures can be varied within a relatively wide range. In general, the reaction is carried out at temperatures of from 0° C. to 150° C., preferably at temperatures of from 20° C. to 110° C.

When carrying out the third step of the process (b) according to the invention, the reaction temperatures can be varied within a relatively wide range. In general, the reaction is carried out at temperatures between −20° C. and +70° C., preferably at temperatures between 0° C. and +50° C.

For carrying out the process (a) according to the invention for preparing compounds of the formula (I-a), in general from 0.8 to 5 mol, preferably from 1 to 3 mol, of alkylating agent of the formula (III-a) or from 0.1 to 1.5 mol, preferably from 0.25 to 1 mol, of Meerwein salt of the formula (III-d) are employed per mole of carboxamide of the formula (II-a).

For carrying out the first step of the process (b) according to the invention for preparing the compounds of the formula (II-b), in general from 0.8 to 1.2 mol, preferably equimolar amounts, of thionating agent are employed per mole of carboxamide of the formula (II-a).

For carrying out the second step of the process (b) according to the invention for preparing the compounds of the formula (I-b) or the formula (I-c), in general from 0.8 to 5 mol, preferably from 1 to 3 mol, of alkylating agent of the formula (III-b) or the formula (III-c) are employed per mole of carboxamide of the formula (II-b).

For carrying out the third step of the process (b) according to the invention for preparing the compounds of the formula (I-d), in general from 0.8 to 1.2 mol, preferably equimolar amounts, of oxidizing agent are employed per mole of carboxamide of the formula (I-c) if the oxidation of the sulphur is to be interrupted at the sulphoxide stage. For oxidation to the sulphone, in general from 1.8 to 3.0 mol, preferably double molar amounts, of oxidizing agent are employed per mole of carboxamide of the formula (I-c).

For carrying out the process (c) according to the invention for preparing the compounds of the formula (I-e) or the formula (I-f), in general from 0.8 to 5 mol, preferably from 1 to 3 mol, of amidating agent of the formula (IV-a) or the formula (IV-b) are employed per mole of carboxamide of the formula (II-b).

The processes according to the invention are generally carried out under atmospheric pressure. However, it is also possible to operate under elevated or reduced pressure—in general between 0.1 bar and 10 bar.

The compounds according to the invention exhibit a potent microbicidal activity and can be employed in crop protection and in the protection of materials for controlling undesirable microorganisms such as fungi and bacteria.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for combating Pseudomonadaceae, Rhizobiaceae, Enterobacteriaceae, Corynebacteriaceae and Streptomycetaceae.

Examples which may be mentioned, but not by limitation, of some pathogens of fungal and bacterial diseases which come under the abovementioned general terms are:

diseases caused by powdery mildew pathogens, such as, for example

Blumeria species such as, for example, Blumeria graminis;
Podosphaera species such as, for example, Podosphaera leucotricha;
Sphaerotheca species such as, for example, Sphaerotheca fuliginea;
Uncinula species such as, for example, Uncinula necator;
diseases caused by rust pathogens such as, for example,
Gymnosporangium species such as, for example, Gymnosporangium sabinae
Hemileia species such as, for example, Hemileia vastatrix;
Phakopsora species such as, for example, Phakopsora pachyrhizi and Phakopsora meibomiae;
Puccinia species such as, for example, Puccinia recondita or Puccinia graminis;
Uromyces species such as, for example, Uromyces appendiculatus;
diseases caused by pathogens from the Oomycetes group such as, for example,
Bremia species such as, for example, Bremia lactucae;
Peronospora species such as, for example, Peronospora pisi or P. brassicae;
Phytophthora species such as, for example, Phytophthora infestans;
Plasmopara species such as, for example, Plasmopara viticola;
Pseudoperonospora species such as, for example, Pseudoperonospora humuli or Pseudoperonospora cubensis;
Pythium species such as, for example, Pythium ultimum;
leaf spot diseases and leaf wilts caused by, for example,
Alternaria species such as, for example, Alternaria solani;
Cercospora species such as, for example, Cercospora beticola;
Cladosporium species such as, for example, Cladosporium cucumerinum;
Cochliobolus species such as, for example, Cochliobolus sativus (conidial form: Drechslera, syn: Helminthosporium);
Colletotrichum species such as, for example, Colletotrichum lindemuthianum;
Cycloconium species such as, for example, Cycloconium oleaginum;
Diaporthe species such as, for example, Diaporthe citri;
Elsinoe species such as, for example, Elsinoe fawcettii;
Gloeosporium species such as, for example, Gloeosporium laeticolor;

*Glomerella* species such as, for example, *Glomerella cingulata*;
*Guignardia* species such as, for example, *Guignardia bidwelli*;
*Leptosphaeria* species such as, for example, *Leptosphaeria maculans*;
*Magnaporthe* species such as, for example, *Magnaporthe grisea*;
*Mycosphaerella* species such as, for example, *Mycosphaerella graminicola* and *Mycosphaerella fijiensis*;
*Phaeosphaeria* species such as, for example, *Phaeosphaeria nodorum*;
*Pyrenophora* species such as, for example, *Pyrenophora teres*;
*Ramularia* species such as, for example, *Ramularia collocygni*;
*Rhynchosporium* species such as, for example, *Rhynchosporium secalis*;
*Septoria* species such as, for example, *Septoria apii*;
*Typhula* species such as, for example, *Typhula incamata*;
*Venturia* species such as, for example, *Venturia inaequalis*;
  root and stem diseases caused by, for example,
*Corticium* species such as, for example, *Corticium graminearum*;
*Fusarium* species such as, for example, *Fusarium oxysporum*;
*Gaeumannomyces* species such as, for example, *Gaeumannomyces graminis*;
*Rhizoctonia* species such as, for example, *Rhizoctonia solani*;
*Tapesia* species such as, for example, *Tapesia acuformis* or *Tapesia yallundae*;
*Thielaviopsis* species such as, for example, *Thielaviopsis basicola*;
  ear and panicle diseases (including maize cobs), caused by, for example,
*Alternaria* species such as, for example, *Alternaria* spp.;
*Aspergillus* species such as, for example, *Aspergillus flavus*;
*Cladosporium* species such as, for example, *Cladosporium cladosporioides*;
*Claviceps* species such as, for example, *Claviceps purpurea*;
*Fusarium* species such as, for example, *Fusarium culmorum*;
*Gibberella* species such as, for example, *Gibberella zeae*;
*Monographella* species such as, for example, *Monographella nivalis*;
  diseases caused by smuts such as, for example,
*Sphacelotheca* species such as, for example, *Sphacelotheca reiliana*;
*Tilletia* species such as, for example, *Tilletia caries*;
*Urocystis* species such as, for example, *Urocystis occulta*;
*Ustilago* species such as, for example, *Ustilago nuda*;
  fruit rots caused by, for example,
*Aspergillus* species such as, for example, *Aspergillus flavus*;
*Botrytis* species such as, for example, *Botrytis cinerea*;
*Penicillium* species such as, for example, *Penicillium expansum* and *Penicillium purpurogenum*;
*Sclerotinia* species such as, for example, *Sclerotinia sclerotiorum*;
*Verticilium* species such as, for example, *Verticilium alboatrum*;
  seed- and soil-borne rot and wilts, and seedling diseases, caused by, for example,
*Fusarium* species such as, for example, *Fusarium culmorum*;
*Phytophthora* species such as, for example, *Phytophthora cactorum*;
*Pythium* species such as, for example, *Pythium ultimum*;
*Rhizoctonia* species such as, for example, *Rhizoctonia solani*;
*Sclerotium* species such as, for example, *Sclerotium rolfsii*;
  cancers, galls and witches' broom disease, caused by, for example,
*Nectria* species such as, for example, *Nectria galligena*;
  wilts caused by, for example,
*Monilinia* species such as, for example, *Monilinia laxa*;
  deformations of leaves, flowers and fruits, caused by, for example,
*Taphrina* species such as, for example, *Taphrina deformans*;
  degenerative diseases of woody species, caused by, for example,
Esca species such as, for example, *Phaeomoniella clamydospora* and *Phaeoacremonium aleophilium* and *Fomitiporia mediterranea*;
  diseases of flowers and seeds, caused by, for example,
*Botrytis* species such as, for example, *Botrytis cinerea*;
  diseases of the plant tubers, caused by, for example,
*Rhizoctonia* species such as, for example, *Rhizoctonia solani*;
*Helminthosporium* species such as, for example, *Helminthosporium solani*;
  diseases caused by bacterial pathogens such as, for example,
*Xanthomonas* species such as, for example, *Xanthomonas campestris* pv. *oryzae*;
*Pseudomonas* species such as, for example, *Pseudomonas syringae* pv. *lachrymans*;
*Erwinia* species such as, for example, *Erwinia amylovora*.

The following diseases of soybeans can preferably be controlled:

Fungal diseases on leaves, stems, pods and seeds caused by, for example, alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*) powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);

fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defences against attack by undesired microorganisms.

Plant-strengthening (resistance-inducing) compounds are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the compounds according to the invention can be employed for protecting plants against attack by the abovementioned pathogens within a certain period of time after the treatment. The period of time within which their protection is effected is generally extended from 1 to 28 days, preferably from 1 to 14 days, particularly preferably from 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example against *Botrytis*, *Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the substances according to the invention can be employed for protecting industrial materials against attack and destruction by undesired microorganisms.

In the present context, industrial materials are understood as meaning non live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:
*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable:

for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example, to improve the activity spectrum or prevent the development of resistance. In many instances, synergistic effects are obtained, i.e. the activity of the mixture exceeds the activity of the individual components.

Examples of co-components in mixtures are the following compounds:
Fungicides:
1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;
2) mitosis and cell division inhibitors: for example benomyl, carbendazim, diethofencarb, ethaboxam, fuberidazole, pencycuron, thiabendazole, thiophanate-methyl, zoxamide;
3) respiration inhibitors (inhibitors of the respiratory chain):
3.1) inhibitors which act on complex I of the respiratory chain: for example diflumetorim;
3.2) inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;
3.3) inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;
4) decouplers: for example dinocap, fluazinam, meptyldinocap;
5) ATP production inhibitors: for example fentin acetate, fentin chloride, fentin hydroxide, silthiofam;
6) amino acid and protein biosynthesis inhibitors: for example andoprim, blasticidin-S, cyprodinil, kasugamycin, kasugamycin hydrochloride hydrate, mepanipyrim, pyrimethanil;
7) signal transduction inhibitors: for example fenpiclonil, fludioxonil, quinoxyfen;
8) lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;
9) inhibitors of ergosterol biosynthesis: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;
10) cell wall synthesis inhibitors: for example benthiavalicarb, dimethomorph, flumorph, iprovalicarb, polyoxins, polyoxorim, validamycin A;
11) melanin biosynthesis inhibitors: for example carpropamid, diclocymet, fenoxanil, phthalide, pyroquilon, tricyclazole;
12) resistance inductors: for example acibenzolar-5-methyl, probenazole, tiadinil;
13) compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;
14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamide, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino)acetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2-(4-chlorophenyl)-N-{2-[3-methoxy-4-(prop-2-yn-1-yloxy)phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidine-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl)methoxy]ethanimidoyl}benzyl)carbamate, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl)ethyl]-2,4-dichloronicotin-amide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N$^2$-(methylsulphonyl)valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl]ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid.

Bactericides:

Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
1. Acetylcholine Esterase (AChE) Inhibitors
1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
1.2 Organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfen-vinphos, chlormephos, chlorpyrifos (-methyl/-ethyl), coumaphos, cyanofenphos, cyanophos, chlorfen-vinphos, demeton-S-methyl, demeton-S-methyl-sulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyra-zofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)
2. Sodium Channel Modulators/Voltage-Dependent Sodium Channel Blockers
2.1 Pyrethroids (for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, trans-fluthrin, ZXI 8901, pyrethrins (pyrethrum))
2.2 Oxadiazines (for Example Indoxacarb)
3. Acetylcholine Receptor Agonists/Antagonists
3.1 Chloronicotinyls/neonicotinoids (for example acetamiprid, clothianidin, dinotefuran, imidacloprid, nitenpyram, nithiazine, thiacloprid, thiamethoxam)
3.2 Nicotine, bensultap, cartap
4. Acetylchuoline Receptor Modulators
4.1 Spinosyns (for example spinosad)
5. GABA-Controlled Chloride Channel Antagonists
5.1 Cyclodiene organochlorines (for example camphechlor, chlordane, endosulfan, gamma-HCH, HCH, heptachlor, lindane, methoxychlor
5.2 Fiproles (for example acetoprole, ethiprole, fipronil, vaniliprole)
6. Chloride Channel Activators
6.1 Mectins (for example abamectin, avermectin, emamectin, emamectin benzoate, ivermectin, milbe-mectin, milbemycin)
7. Juvenile Hormone Mimetics
(for example diofenolan, epofenonane, fenoxycarb, hydroprene, kinoprene, methoprene, pyriproxifen, triprene)
8. Ecdysone Agonists/Disruptors
8.1 Diacylhydrazines (for example chromafenozide, halofenozide, methoxyfenozide, tebufenozide)
9. Chitin Biosynthesis Inhibitors
9.1 Benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, tri-flumuron)
9.2 Buprofezin
9.3 Cyromazine
10. Inhibitors of Oxidative Phosphorylation, ATP Disruptors
10.1 Diafenthiuron
10.2 Organotins (for example azocyclotin, cyhexatin, fenbutatin oxide)
11. Uncouplers of Oxidative Phosphorylation by Interrupting the H-Proton Gradient
11.1 Pyrroles (for example chlorfenapyr)
11.2 Dinitrophenols (for example binapacyrl, dinobuton, dinocap, DNOC)
12. Site-I Electron Transport Inhibitors
12.1 METIs (for example fenazaquin, fenpyroximate, pyrimidifen, pyridaben, tebufenpyrad, tolfenpyrad)

12.2 Hydramethylnone
12.3 Dicofol
13. Site-II Electron Transport Inhibitors
13.1 Rotenone
14. Site-III Electron Transport Inhibitors
14.1 Acequinocyl, fluacrypyrim
15. Microbial Disruptors of the Insect Gut Membrane
   *Bacillus thuringiensis* strains
16. Fat Synthesis Inhibitors
16.1 Tetronic acids (for example spirodiclofen, spiromesifen)
16.2 Tetramic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1)]
17. Carboxamides
   (for example flonicamid)
18. Octopaminergic Agonists
   (for example amitraz)
19. Inhibitors of Magnesium-stimulated ATPase
   (for example propargite)
20. Ryanodin Receptor Agonists,
20.1 Benzoic acid dicarboxamides
   [for example $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg. No.: 272451-65-7), flubendiamide]
20.2 Anthranilamides (for example DPX E2Y45=3-bromo-N-{4-chloro-2-methyl-6-[(methylamino)-carbonyl]phenyl}-1-(3-chloropyridin-2-yl)-1H-pyrazole-5-carboxamide)
21. Nereistoxin Analogues
   (for example thiocyclam hydrogen oxalate, thiosultap sodium)
22. Biologicals, Hormones or Pheromones
   (for example azadirachtin, *Bacillus* spec., *Beauveria* spec., codlemone, *Metarrhizium* spec., *Paecilomyces* spec., thuringiensin, *Verticillium* spec.)
23. Active Compounds with Unknown or Unspecific Mechanisms of Action
23.1 Fumigants (for example aluminium phosphide, methyl bromide, sulphuryl fluoride)
23.2 Selective antifeedants (for example cryolite, flonicamid, pymetrozine)
23.3 Mite growth inhibitors (for example clofentezine, etoxazole, hexythiazox)
23.4 Amidoflumet, benclothiaz, benzoximate, bifenazate, bromopropylate, buprofezin, quino-methionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methyl-phenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plant can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, breeds, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, more developed root system, higher resistance of the plant variety or plant cultivar, increased growth of shoots, higher plant vitality, increased tolerance to high or low temperatures, increased tolerance to drought or to water or soil salinity, increased flowering performance, easier harvesting, accelerated maturation, higher harvest yields, larger fruit, increased plant size, greener leaf colour, earlier blossoming, better quality and/or a higher nutritional value of the harvested products, higher sugar concentration in the fruits, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defence of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

Preparation Examples

Preparation of Compound 9

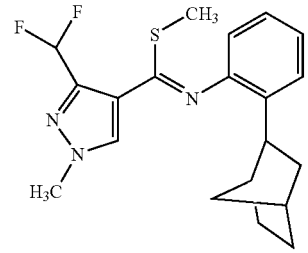

At 0° C., 0.1 g (3.6 mmol) of sodium hydride (80% pure) and 1.2 g (8.3 mmol) of methyl iodide in 5 ml of dimethylformamide are added to a solution consisting of 1.0 g (2.8 mmol) of N-(2-bicyclo[2.2.1]hept-2-ylphenyl)-3-(difluoromethyl)-1-methyl-1H-pyrazole-4-thiocarboxamide in 10 ml of dimethylformamide. The reaction mixture is slowly warmed to room temperature and stirred at this temperature for 1 hour. For work-up, the reaction mixture is poured into water and extracted three times with in each case 50 ml of ethyl acetate. The combined organic phases are washed with saturated sodium chloride solution, dried over sodium sulphate and concentrated under reduced pressure. Column chromatography (cyclohexane/ethyl acetate 4:1) gives 0.7 g (1.9 mmol, 67% of theory) of methyl N-(2-bicyclo[2.2.1]hept-2-ylphenyl)-3-(difluoromethyl)-1-methyl-1H-pyrazole-4-carbimidothioate [logP (pH 2.3)=4.75].

Analogous to this example and in accordance with the general descriptions of the processes according to the invention, it is possible to obtain the compounds of the formula (I) listed in Table I below.

TABLE 1

(I)

| No. | X | M | Q | Z | A | logP (pH 2.3) |
|-----|---|---|---|---|---|---------------|
| 1 | SO$_2$CH$_3$ | M-1, R$^7$ = H | direct bond | | | |
| 2 | SCH$_2$CH(OCH$_3$)$_2$ | M-1, R$^7$ = H | direct bond | | | |
| 3 | S(CH$_2$)$_2$OCH$_3$ | M-1, R$^7$ = H | direct bond | | | 4.62 |
| 4 | S(CH$_2$)$_3$OH | M-1, R$^7$ = H | direct bond | | | |
| 5 | SCH$_2$C(O)NHCH$_3$ | M-1, R$^7$ = H | direct bond | | | |
| 6 | SCH$_2$CN | M-1, R$^7$ = H | direct bond | | | 4.15 |

TABLE 1-continued (I)

| No. | X | M | Q | Z | A | logP (pH 2.3) |
|---|---|---|---|---|---|---|
| 7 | SCH$_2$SCN | M-1, R$^7$ = H | direct bond | | pyrazole-bicyclic group with CF$_2$, 4-methyl, N-CH$_3$ | 4.55 |
| 8 | SCH$_2$C≡CH | M-1, R$^7$ = H | direct bond | | pyrazole-bicyclic group with CF$_2$, 4-methyl, N-CH$_3$ | 4.65 |
| 9 | SCH$_3$ | M-1, R$^7$ = H | direct bond | | pyrazole-bicyclic group with CF$_2$, 4-methyl, N-CH$_3$ | 4.75 |
| 10 | S(CH$_2$)$_2$OH | M-1, R$^7$ = H | direct bond | | pyrazole-bicyclic group with CF$_2$, 4-methyl, N-CH$_3$ | 3.23 |
| 11 | SCH$_2$CO$_2$C$_2$H$_5$ | M-1, R$^7$ = H | direct bond | | pyrazole-bicyclic group with CF$_2$, 4-methyl, N-CH$_3$ | 4.66 |
| 12 | 2-chloro-5-(methylthiomethyl)pyridine | M-1, R$^7$ = H | direct bond | | pyrazole-bicyclic group with CF$_2$, 4-methyl, N-CH$_3$ | 4.95 |

TABLE 1-continued
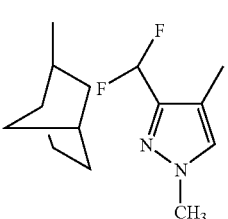
(I)
| No. | X | M | Q | Z | A | logP (pH 2.3) |
|---|---|---|---|---|---|---|
| 13 | S(CH$_2$)$_{11}$CH$_3$ | M-1, R$^7$ = H | direct bond | | 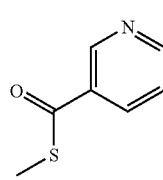 | 7.36 |
| 14 | 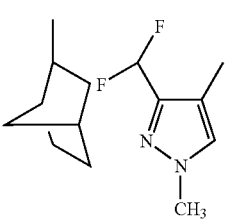 | M-1, R$^7$ = H | direct bond | | 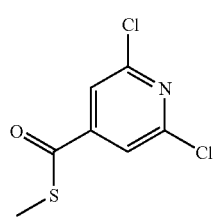 | |
| 15 | 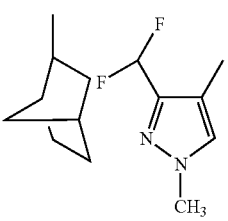 | M-1, R$^7$ = H | direct bond | | 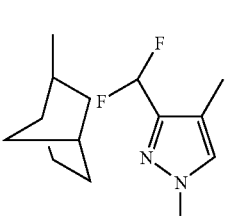 | |
| 16 | SC(O)CH$_2$OCH$_3$ | M-1, R$^7$ = H | direct bond | | 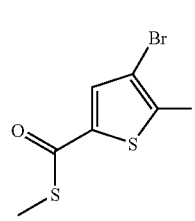 | |
| 17 | 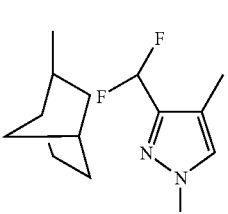 | M-1, R$^7$ = H | direct bond | | | |

TABLE 1-continued (I)

| No. | X | M | Q | Z | A | logP (pH 2.3) |
|---|---|---|---|---|---|---|
| 18 | SC(O)C(CH₃)₃ | M-1, R⁷ = H | direct bond | | | 5.81 |
| 19 | | M-1, R⁷ = H | direct bond | | | 6.52 |
| 20 | | M-1, R⁷ = H | direct bond | | | 6.66 |

Preparation of Starting Materials of the Formula (II-a)

Preparation of Compound (II-7)

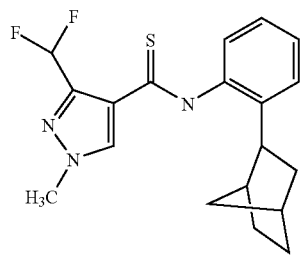

0.3 g (1.4 mmol) of phosphorus pentasulphide is added to a solution consisting of 0.48 g (1.4 mmol) of N-(2-bicyclo[2.2.1]hept-2-ylphenyl)-3-(difluoromethyl)-1-methyl-1H-pyrazole-4-carboxamide in 20 ml of toluene, and the reaction mixture is stirred at 70° C. for 2 hours. For work-up, the reaction mixture is poured into water and extracted once with 20 ml of toluene and twice with in each case 20 ml of ethyl acetate. The combined organic phases are dried over sodium sulphate and concentrated under reduced pressure. Column chromatography (gradient cyclohexane/ethyl acetate) gives 0.32 g (0.89 mmol, 63% of theory) of N-(2-bicyclo[2.2.1]hept-2-ylphenyl)-3-(difluoromethyl)-1-methyl-1H-pyrazole-4-thiocarboxamide [logP (pH 2.3)=3.66].

Preparation of Compound (II-8)

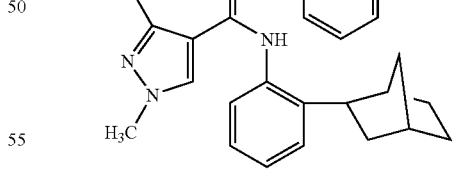

0.9 g (8.4 mmol) of phenylhydrazine in 10 ml of dimethylformamide is added to a solution consisting of 1.0 g (2.7 mmol) of N-(2-bicyclo[2.2.1]hept-2-ylphenyl)-3-(difluoromethyl)-1-methyl-1H-pyrazole-4-thiocarboxamide in 10 ml of methanol. The reaction mixture is stirred at 70° C. for 16 hours. For work-up, the reaction mixture is poured into water and extracted three times with in each case 20 ml of dichloromethane. The combined organic phases are dried over sodium sulphate and concentrated under reduced pressure. Column chromatography (gradient cyclohexane/ethyl acetate) gives 0.42 g (0.96 mmol, 35% of theory) of N-(2-bicyclo[2.2.1]hept-2-ylphenyl)-3-(difluoromethyl)-1-methyl-N'-phenyl-1H-pyrazole-4-carbohydrazonamide [logP (pH 2.3)=3.66].

Analogously to this example and in accordance with the general descriptions of the processes according to the invention, it is possible to obtain the compounds of the formula (III) listed in Table 2 below.

TABLE 2

(II-a)

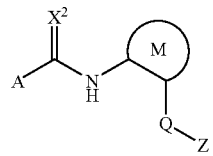

| No. | X | M | Q | Z | A | logP (pH 2.3) |
|---|---|---|---|---|---|---|
| II-1 | S | M-1, $R^7$ = H | direct bond | G5 | | 3.70 (at pH 7.5) |
| II-2 | S | M-1, $R^7$ = 4-F | direct bond | | | |
| II-3 | N—$OCH_3$ | M-1, $R^7$ = H | direct bond | | | |
| II-4 | N—$CH_3$ | M-1, $R^7$ = H | direct bond | | | |
| II-5 | N—$NH_2$ | M-1, $R^7$ = H | direct bond | | | |

TABLE 2-continued (II-a)

| No. | X | M | Q | Z | A | logP (pH 2.3) |
|-----|---|---|---|---|---|---------------|
| II-6 | N—N(CH$_3$)$_2$ | M-1, R$^7$ = H | direct bond | (norbornyl) | (3-(CHF$_2$)-4-methyl-1-methylpyrazole) | |
| II-7 | S | M-1, R$^7$ = H | direct bond | (norbornyl) | (3-(CHF$_2$)-4-methyl-1-methylpyrazole) | 3.66 |
| II-8 | HN–N(phenyl) | M-1, R$^7$ = H | direct bond | (norbornyl) | (3-(CHF$_2$)-4-methyl-1-methylpyrazole) | 3.66 |
| II-9 | N—OH | M-1, R$^7$ = H | direct bond | (norbornyl) | (3-(CHF$_2$)-4-methyl-1-methylpyrazole) | 2.88 |

The logP values given in the Tables and Preparation Examples above are determined in accordance with EEC Directive 79/831 Annex V.A8 by HPLC (High Performance Liquid Chromatography) on a reversed-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile. The determination is carried out in the neutral range at pH 7.5 using the mobile phases 0.01-molar aqueous phosphate buffer solution and acetonitrile; linear gradient from 10% acetonitrile to 90% acetonitrile.

Calibration is carried out using unbranched alkan-2-ones (having 3 to 16 carbon atoms), with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Sphaerotheca* Test (Cucumber)/Protective

| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

TABLE A

Sphaerotheca Test (cucumber)/protective

| Active compound according to the invention | Application rate of active compound in ppm | Efficacy in % |
|---|---|---|
| (10) 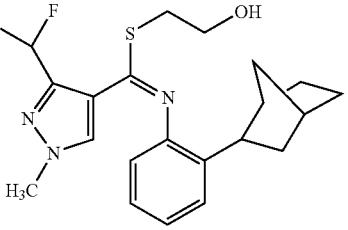 | 100 | 100 |
| (11) 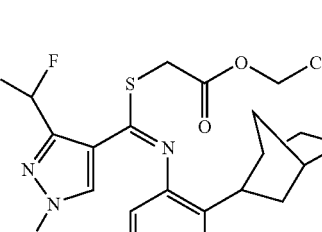 | 100 | 100 |
| (20) 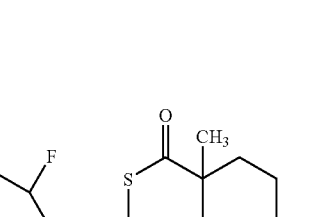 | 100 | 100 |

Example B

*Venturia* Test (Apple)/Protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier and the concentrate is diluted with water to the desired concentration. To test for protective activity, young plants are sprayed with the active compound preparation at the stated application rates. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day. The plants are then placed in a greenhouse at about 21° C. and a relative atmospheric humidity of about 90%. Evaluation is carried out 10 days after the inoculation. 0% means an efficacy which corresponds to that of the control, whereas an efficacy of 100% means that no infection is observed.

TABLE B

Venturia Test (apple)/protective

| Active compound according to the invention | Application rate of active compound in ppm | Efficacy in % |
|---|---|---|
| (10) [structure] | 100 | 100 |
| (11) [structure] | 100 | 100 |
| (19) [structure] | 100 | 99 |
| (20) [structure] | 100 | 100 |

Example C

*Botrytis* Test (Bean)/Protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier and the concentrate is diluted with water to the desired concentration. To test for protective activity, young plants are sprayed with the active compound preparation at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity. The size of the infected areas on the leaves is evaluated 2 days after the inoculation. 0% means an efficacy which corresponds to that of the control, whereas an efficacy of 100% means that no infection is observed.

TABLE C

Botrytis Test (bean)/protective

| Active compound according to the invention | Application rate of active compound in ppm | Efficacy in % |
|---|---|---|
| (10) [structure: difluoromethyl pyrazole with S-CH2CH2-OH, N-methyl, phenyl with bicyclic substituent] | 250 | 100 |
| (11) [structure: difluoromethyl pyrazole with S-CH2-C(O)-O-CH2CH3, N-methyl, phenyl with bicyclic substituent] | 250 | 100 |

Example D

Uromyces Test (Bean)/Protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier and the concentrate is diluted with water to the desired concentration. To test for protective activity, young plants are sprayed with the active compound preparation at the stated application rate. After the spray coating has dried on, the plants are inoculated with an aqueous spore suspension of the bean rust pathogen *Uromyces appendiculatus* and then remain in an incubation cabinet at about 20° C. and 100% relative atmospheric humidity for 1 day. The plants are then placed in a greenhouse at about 21° C. and a relative atmospheric humidity of about 90%. Evaluation is carried out 10 days after the inoculation. 0% means an efficacy which corresponds to that of the control, whereas an efficacy of 100% means that no infection is observed.

TABLE D

Uromyces Test (bean)/protective

| Active compound according to the invention | Application rate of active compound in ppm | Efficacy in % |
|---|---|---|
| (10) [structure: difluoromethyl pyrazole with S-CH2CH2-OH, N-methyl, phenyl with bicyclic substituent] | 100 | 100 |
| (11) [structure: difluoromethyl pyrazole with S-CH2-C(O)-O-CH2CH3, N-methyl, phenyl with bicyclic substituent] | 100 | 100 |

TABLE D-continued

Uromyces Test (bean)/protective

| Active compound according to the invention | Application rate of active compound in ppm | Efficacy in % |
|---|---|---|
| (19) 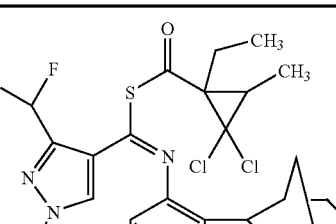 | 100 | 96 |
| (20) | 100 | 99 |

Example E

Alternaria Test (Tomato)/Protective

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier and the concentrate is diluted with water to the desired concentration. To test for protective activity, young tomato plants are sprayed with the active compound preparation at the stated application rate. 1 day after the treatment, the plants are inoculated with a spore suspension of *Alternaria solani* and then remain at 100% relative atmospheric humidity and 20° C. for 24 h. The plants then remain at 96% relative atmospheric humidity and a temperature of 20° C. Evaluation is carried out 7 days after the inoculation. 0% means an efficacy which corresponds to that of the control, whereas an efficacy of 100% means that no infection is observed.

TABLE E

Alternaria Test (tomato)/protective

| Active compound according to the invention | Application rate of active compound in ppm | Efficacy in % |
|---|---|---|
| (10) | 500 | 100 |
| (11) | 500 | 95 |

TABLE E-continued

Alternaria Test (tomato)/protective

| Active compound according to the invention | Application rate of active compound in ppm | Efficacy in % |
|---|---|---|
| (19) [structure] | 500 | 90 |
| (20) [structure] | 500 | 80 |

Example F

*Pyrenophora teres* Test (Barley)/Protective

| Solvent: | 50 parts by weight of N,N-dimethylacetamide |
|---|---|
| Emulsifier: | 1 part by weight of alkylaryl polyglycol ether |

To produce a suitable preparation of active compound, 1 part by weight of active compound is mixed with the stated amounts of solvent and emulsifier and the concentrate is diluted with water to the desired concentration. To test for protective activity, young plants are sprayed with the active compound preparation at the stated application rate. After the spray coating has dried on, the plants are sprayed with a conidia suspension of *Pyrenophora teres*. The plants remain in an incubation cabin at 20° C. and 100% relative atmospheric humidity for 48 hours. The plants are then placed in a greenhouse at a temperature of about 20° C. and a relative atmospheric humidity of about 80%. Evaluation is carried out 8 days after the inoculation. 0% means an efficacy which corresponds to that of the control, whereas an efficacy of 100% means that no infection is observed.

TABLE F

*Pyrenophora teres* Test (barley)/protective

| Active compound according to the invention | Application rate of active compound in ppm | Efficacy in % |
|---|---|---|
| (11) [structure] | 1000 | 100 |

TABLE F-continued

Pyrenophora teres Test (barley)/protective

| Active compound according to the invention | | Application rate of active compound in ppm | Efficacy in % |
|---|---|---|---|
| (19) | 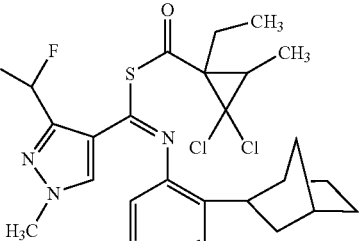 | 1000 | 92 |
| (20) | | 1000 | 100 |

Example G

Puccinia Test (Wheat)/Protective

| | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amounts of solvent and emulsifier and the concentrate is diluted with water to the desired concentration. To test for protective activity, young plants are sprayed with the active compound preparation at the stated application rate. After the spray coating has dried on, the plants are sprayed with a conidia suspension of *Puccinia recondita*. The plants remain in an incubation cabin at 20° C. and 100% relative atmospheric humidity for 48 hours. The plants are then placed in a greenhouse at a temperature of about 20° C. and a relative atmospheric humidity of about 80% to promote the development of rust pustules. Evaluation is carried out 10 days after the inoculation. 0% means an efficacy which corresponds to that of the control, whereas an efficacy of 100% means that no infection is observed.

TABLE G

Puccinia Test (wheat)/protective

| Active compound according to the invention | | Application rate of active compound in ppm | Efficacy in % |
|---|---|---|---|
| (11) | 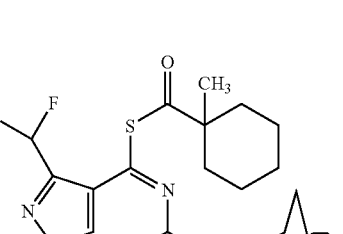 | 1000 | 100 |

TABLE G-continued

Puccinia Test (wheat)/protective

| Active compound according to the invention | Application rate of active compound in ppm | Efficacy in % |
| --- | --- | --- |
| (19) 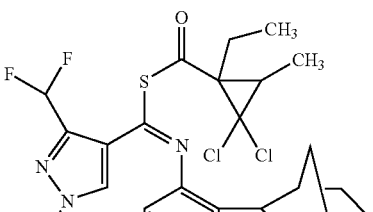 | 1000 | 93 |
| (20) 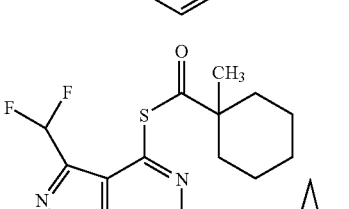 | 1000 | 100 |

The invention claimed is:
1. A compound of formula (I)

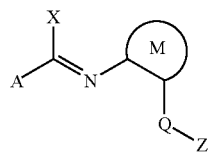

in which
X represents $OR^1$, $SR^2$, $NHR^3$, $NR^4R^5$, $SOR^6$, $SO_2R^6$,
$R^1$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl,
$R^2$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), —$CH_2S$—CN, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl,
$R^3$, $R^4$ and $R^5$ independently of one another represent amino, hydroxyl, cyano, $C_1$-$C_{12}$-alkyl, $C_1$-$C_8$-alkoxy, $C_2$-$C_8$-alkenyl, $C_2$-$C_8$-alkynyl, $C_1$-$C_6$-alkylamino, di($C_1$-$C_6$-alkyl)amino, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), phenoxy, phenylamino, benzyloxy or benzylamino,
$R^6$ represents $C_1$-$C_{12}$-alkyl or $C_1$-$C_8$-haloalkyl,
M represents a phenyl which is monosubstituted by $R^7$,
$R^7$ represents hydrogen, fluorine, chlorine, methyl, isopropyl, methylthio or trifluoromethyl,
Q represents a direct bond, $C_1$-$C_4$-alkylene, $C_2$-$C_4$-alkenylene, O, S, SO, $SO_2$ or $NR^9$,
$R^9$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl or $C_3$-$C_6$-cycloalkyl,
Z represents $Z^1$, $Z^2$, $Z^3$, $Z^4$, $Z^5$ or $Z^6$,
$Z^1$ represents phenyl which is optionally mono- to pentasubstituted by identical or different substituents,
$Z^2$ represents pyridinyl which is optionally mono- to trisubstituted by identical or different substituents,
$Z^3$ represents cycloalkyl or bicycloalkyl, each of which is optionally mono- or polysubstituted by identical or different halogen, alkyl and/or —$(CR^{10}R^{11})_m SiR^{12}R^{13}R^{14}$ substituents,
$Z^4$ represents unsubstituted $C_2$-$C_{20}$-alkyl or represents $C_1$-$C_{20}$-alkyl which is mono- or polysubstituted by identical or different halogen, alkylthio, alkylsulphinyl, alkylsulphonyl, alkoxy, alkylamino, dialkylamino, haloalkylthio, haloalkyl-sulphinyl, haloalkylsulphonyl, haloalkoxy, haloalkylamino, halodialkylamino, —$SiR^{12}R^{13}R^{14}$ and/or $C_3$-$C_6$-cycloalkyl substituents, where the cycloalkyl moiety for its part may optionally be mono- or polysubstituted by identical or different halogen and/or $C_1$-$C_4$-alkyl substituents,
$Z^5$ represents $C_2$-$C_{20}$-alkenyl or $C_2$-$C_{20}$-alkynyl, each of which is optionally mono- or polysubstituted by identical or different halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^{12}$R$^{13}$R$^{14}$ and/or C$_3$-C$_6$-cycloalkyl substituents, where the cycloalkyl moiety for its part may optionally be mono- or polysubstituted by identical or different halogen and/or C$_1$-C$_4$-alkyl substituents, Z$^6$ represents an optionally mono- or polysubstituted saturated or unsaturated 3- to 7-membered ring which contains a silicon atom as ring member, in which case Q represents a direct bond or C$_1$-C$_4$-alkylene, R$^{10}$ represents hydrogen or C$_1$-C$_4$-alkyl, R$^{11}$ represents hydrogen or C$_1$-C$_4$-alkyl, m represents 0, 1, 2 or 3, R$^{12}$ and R$^{13}$ independently of one another represent hydrogen, C$_1$-C$_8$-alkyl, C$_1$-C$_8$-alkoxy, C$_1$-C$_4$-alkoxy-C$_1$-C$_4$-alkyl, C$_1$-C$_4$-alkylthio-C$_1$-C$_4$-alkyl or C$_1$-C$_6$-haloalkyl, R$^{14}$ represents hydrogen, C$_1$-C$_8$-alkyl, C$_1$-C$_8$-alkoxy, C$_1$-C$_4$-alkoxy-C$_1$-C$_4$-alkyl, C$_1$-C$_4$-alkylthio-C$_1$-C$_4$-alkyl, C$_2$-C$_8$-alkenyl, C$_2$-C$_8$-alkynyl, C$_1$-C$_6$-haloalkyl, C$_2$-C$_6$-haloalkenyl, C$_2$-C$_6$-haloalkynyl, C$_3$-C$_6$-cycloalkyl, or represents in each case optionally substituted phenyl or phenylalkyl, A represents one of the radicals selected from the group consisting of A1, A2, A3, A9, A11, A12, A13, A14, A15, A18, and A19

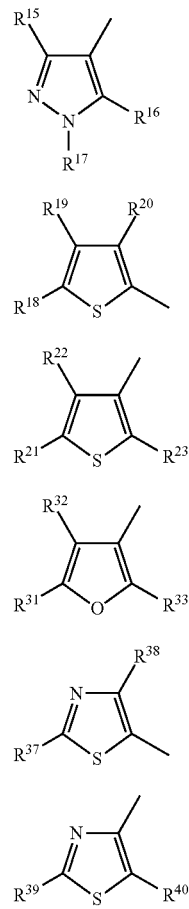

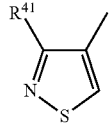
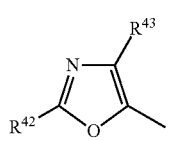
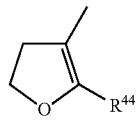
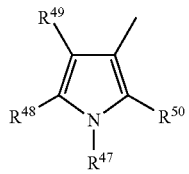
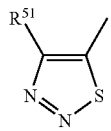

R$^{15}$ represents hydrogen, cyano, halogen, nitro, C$_1$-C$_4$-alkyl, C$_1$-C$_4$-alkoxy, C$_1$-C$_4$-alkylthio, C$_3$-C$_6$-cycloalkyl, C$_1$-C$_4$-haloalkyl, C$_1$-C$_4$-haloalkoxy or C$_1$-C$_4$-halo-alkylthio having in each case 1 to 5 halogen atoms, aminocarbonyl or amino-carbonyl-C$_1$-C$_4$-alkyl, R$^{16}$ represents hydrogen, halogen, cyano, C$_1$-C$_4$-alkyl, C$_1$-C$_4$-alkoxy or C$_1$-C$_4$-alkylthio, R$^{17}$ represents hydrogen, C$_1$-C$_4$-alkyl, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkoxy-C$_1$-C$_4$-alkyl, C$_1$-C$_4$-haloalkyl, C$_1$-C$_4$-haloalkylthio-C$_1$-C$_4$-alkyl, C$_1$-C$_4$-haloalkoxy-C$_1$-C$_4$-alkyl having in each case 1 to 5 halogen atoms, or phenyl, R$^{18}$ and R$^{19}$ independently of one another, represent hydrogen, halogen, C$_1$-C$_4$-alkyl or C$_1$-C$_4$-haloalkyl having 1 to 5 halogen atoms, R$^{20}$ represents halogen, cyano or C$_1$-C$_4$-alkyl, or C$_1$-C$_4$-haloalkyl or C$_1$-C$_4$-haloalkoxy having in each case 1 to 5 halogen atoms, R$^{21}$ and R$^{22}$ independently of one another represent hydrogen, halogen, C$_1$-C$_4$-alkyl or C$_1$-C$_4$-haloalkyl having 1 to 5 halogen atoms, R$^{23}$ represents hydrogen, halogen, C$_1$-C$_4$-alkyl or C$_1$-C$_4$-haloalkyl having 1 to 5 halogen atoms, R$^{31}$ and R$^{32}$ independently of one another represent hydrogen, halogen, amino, C$_1$-C$_4$-alkyl or C$_1$-C$_4$-haloalkyl having 1 to 5 halogen atoms, R$^{33}$ represents hydrogen, halogen, C$_1$-C$_4$-alkyl or C$_1$-C$_4$-haloalkyl having 1 to 5 halogen atoms, R$^{37}$ represents hydrogen, halogen, amino, C$_1$-C$_4$-alkylamino, di-(C$_1$-C$_4$-alkyl)amino, cyano, C$_1$-C$_4$-alkyl or C$_1$-C$_4$-haloalkyl having 1 to 5 halogen atoms, R$^{38}$ represents halogen, C$_1$-C$_4$-alkyl or C$_1$-C$_4$-haloalkyl having 1 to 5 halogen atoms, $R^{39}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{40}$ represents halogen, $C_1$-$C_4$-alkyl or $C_1$-$C_4$-haloalkyl having 1 to 5 halogen atoms, $R^{41}$ represents halogen, $C_1$-$C_4$-alkyl or $C_1$-$C_4$-haloalkyl having 1 to 5 halogen atoms, $R^{42}$ represents hydrogen or $C_1$-$C_4$-alkyl, $R^{43}$ represents halogen or $C_1$-$C_4$-alkyl, $R^{44}$ represents $C_1$-$C_4$-alkyl or $C_1$-$C_4$-haloalkyl having 1 to 5 halogen atoms, $R^{47}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{48}$ represents hydrogen, halogen, $C_1$-$C_4$-alkyl or $C_1$-$C_4$-haloalkyl having 1 to 5 halogen atoms, $R^{49}$ represents hydrogen, halogen, cyano, $C_1$-$C_4$-alkyl or $C_1$-$C_4$-haloalkyl having 1 to 5 halogen atoms, $R^{50}$ represents hydrogen, halogen, $C_1$-$C_4$-alkyl or $C_1$-$C_4$-haloalkyl having 1 to 5 halogen atoms, $R^{51}$ represents $C_1$-$C_4$-alkyl.

2. A process for preparing a compound according to claim 1, comprising (a) if X represents $OR^1$, reacting a compound of formula (II-a)

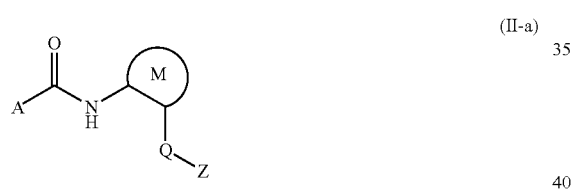

(II-a)

if appropriate, in the presence of a base, with an alkylating agent of the formula (III-a)

$LG^1$-$R^1$ (III-a)

in which $LG^1$ represents a leaving group or with a Meerwein salt of the formula (III-d)

$(R^1)_3O^+E^-$ (III-d)

in which

E represents $BF_4$, $SbF_6$ or $SbCl_6$, to give a compound of formula (I-a)

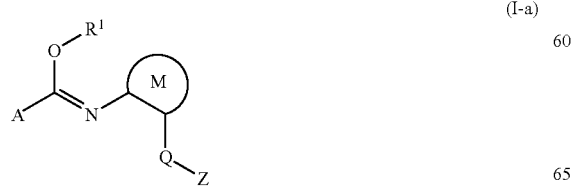

(I-a)

(b) if X represents $SR^2$, $SOR^6$ or $SO_2R^6$, in a first step reacting the compound of formula (II-a)

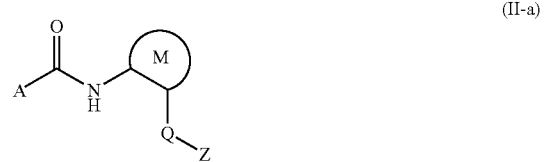

(II-a)

if appropriate in the presence of a diluent, with a thionating agent, thus giving a compound of formula (II-b)

(II-b)

and, in a second step, if appropriate in the presence of a base, reacting with an alkylating agent of the formula (III-b) or the formula (III-c)

$LG^2$-$R^2$ (III-b)

$LG^6$-$R^6$ (III-c)

in which $LG^2$ represents a leaving group, $LG^6$ represents a leaving group, to give a compound of formula (I-b) or the formula (I-c)

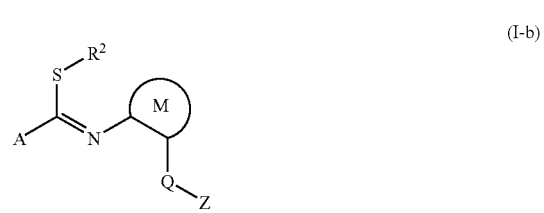

(I-b)

(I-c)

and, in a third step, reacting the compound of formula (I-c) with an oxidizing agent, if appropriate in the presence of a diluent, if appropriate in the presence of an acid binder and if appropriate in the presence of a catalyst, thus giving a compound of formula (I-d)

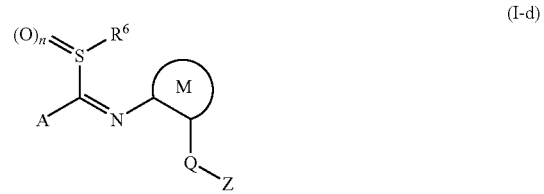

(I-d)

in which n represents 1 or 2, (c) if X represents NHR³ or NR⁴R⁵, reacting the compound of formula (II-b)

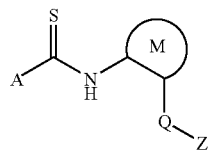
(II-b)

if appropriate in the presence of a base, with an amidating agent of formula (IV-a) or formula (IV-b)

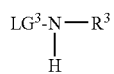
(IV-a)

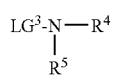
(IV-b)

in which
LG³ represents a leaving group,
to give a compound of formula (I-e) or formula (I-f)

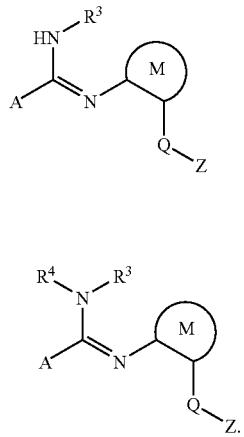
(I-e)

(I-f)

3. A compound of formula (I) according to claim 1:

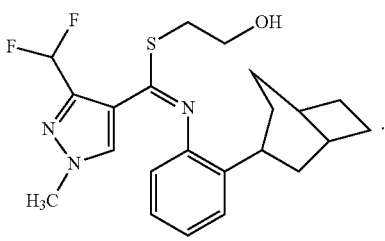

4. A composition for controlling unwanted microorganisms, comprising at least one compound according to claim 3, and an extender and/or surfactant.

5. A compound according to claim 1 of the formulae (I-a), (I-b), (I-e), (I-f) or (I-d)

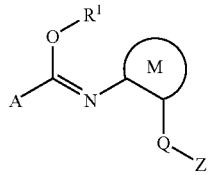
(I-a)

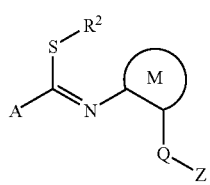
(I-b)

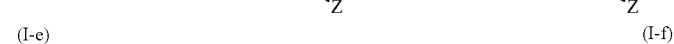
(I-e)

(I-f)

(I-d)

in which
n represents 1 or 2.

6. A composition for controlling unwanted microorganisms, comprising at least one-compound according to claim 1, and an extender and/or surfactant.

7. A compound of the formula (I) according to claim 1 that is used for controlling unwanted microorganisms.

8. A method for controlling unwanted microorganisms, comprising applying a compound according to claim 1 to microorganisms and/or a habitat thereof.

9. A process for preparing a composition for controlling unwanted microorganisms, comprising mixing a compound according to claim 1 with an extender and/or surfactant.

10. A compound of the formula (I) according to claim 1, wherein A represents one of the radicals selected from the group consisting of A1, A2, A3, A9, A11, A12, A13, A14, A15, and A18.

11. A composition for controlling unwanted microorganisms, comprising at least one compound of formula (I)

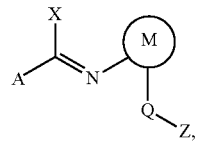

and an extender and/or surfactant,
wherein
X represents $OR^1$, $SR^2$, $NHR^3$, $NR^4R^5$, $SOR^6$, $SO_2R^6$,
$R^1$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl,
$R^2$ represents $C_1$-$C_{12}$-alkyl, $C_2$-$C_8$-alkenyl, $C_2$-$C_8$-alkynyl, $C_1$-$C_8$-haloalkyl, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), —$CH_2S$—CN, ($C_1$-$C_4$-alkoxy)carbonyl-($C_1$-$C_4$-alkyl); in each case optionally halogen-, $C_1$-$C_4$-alkyl- or $C_1$-$C_4$-haloalkyl-substituted phenyl-($C_1$-$C_2$-alkyl) or hetaryl-($C_1$-$C_2$-alkyl); in each case optionally $C_1$-$C_4$-alkoxy-, halogen-, $C_1$-$C_4$-alkyl- or $C_1$-$C_4$-haloalkyl-substituted ($C_1$-$C_6$-alkyl)carbonyl, ($C_3$-$C_8$-cycloalkyl)carbonyl, phenylcarbonyl or hetarylcarbonyl,
$R^3$, $R^4$ and $R^5$ independently of one another represent amino, hydroxyl, cyano, $C_1$-$C_{12}$-alkyl, $C_1$-$C_8$-alkoxy, $C_2$-$C_8$-alkenyl, $C_2$-$C_8$-alkynyl, $C_1$-$C_6$-alkylamino, di($C_1$-$C_6$-alkyl)amino, hydroxy-$C_1$-$C_8$-alkyl, ($C_1$-$C_4$-alkoxy)-$C_1$-$C_8$-alkyl, bis($C_1$-$C_4$-alkoxy)-$C_1$-$C_8$-alkyl, cyano-($C_1$-$C_4$-alkyl), phenoxy, phenylamino, benzyloxy or benzylamino,
$R^6$ represents $C_1$-$C_{12}$-alkyl or $C_1$-$C_8$-haloalkyl,
M represents a phenyl which is monosubstituted by $R^7$,
$R^7$ represents hydrogen, fluorine, chlorine, methyl, isopropyl, methylthio or trifluoromethyl,
Q represents a direct bond, $C_1$-$C_4$-alkylene, $C_2$-$C_4$-alkenylene, O, S, SO, $SO_2$ or $NR^9$,
$R^9$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl or $C_3$-$C_6$-cycloalkyl,
Z represents $Z^1$, $Z^2$, $Z^3$, $Z^4$, $Z^5$ or $Z^6$,
$Z^1$ represents phenyl which is optionally mono- to pentasubstituted by identical or different substituents,
$Z^2$ represents pyridinyl which is optionally mono- to trisubstituted by identical or different substituents,
$Z^3$ represents cycloalkyl or bicycloalkyl, each of which is optionally mono- or polysubstituted by identical or different halogen, alkyl and/or —$(CR^{10}R^{11})_m SiR^{12}R^{13}R^{14}$ substituents,
$Z^4$ represents unsubstituted $C_2$-$C_{20}$-alkyl or represents $C_1$-$C_{20}$-alkyl which is mono- or polysubstituted by identical or different halogen, alkylthio, alkylsulphinyl, alkylsulphonyl, alkoxy, alkylamino, dialkylamino, haloalkylthio, haloalkyl-sulphinyl, haloalkylsulphonyl, haloalkoxy, haloalkylamino, halodialkylamino, —$SiR^{12}R^{13}R^{14}$ and/or $C_3$-$C_6$-cycloalkyl substituents, where the cycloalkyl moiety for its part may optionally be mono- or polysubstituted by identical or different halogen and/or $C_1$-$C_4$-alkyl substituents,
$Z^5$ represents $C_2$-$C_{20}$-alkenyl or $C_2$-$C_{20}$-alkynyl, each of which is optionally mono- or polysubstituted by identical or different halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^{12}R^{13}R^{14}$ and/or $C_3$-$C_6$-cycloalkyl substituents, where the cycloalkyl moiety for its part may optionally be mono- or polysubstituted by identical or different halogen and/or $C_1$-$C_4$-alkyl substituents,
$Z^6$ represents an optionally mono- or polysubstituted saturated or unsaturated 3- to 7-membered ring which contains a silicon atom as ring member, in which case Q represents a direct bond or $C_1$-$C_4$-alkylene,
$R^{10}$ represents hydrogen or $C_1$-$C_4$-alkyl,
$R^{11}$ represents hydrogen or $C_1$-$C_4$-alkyl,
m represents 0, 1, 2 or 3,
$R^{12}$ and $R^{13}$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl,
$R^{14}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl,
A represents one of the radicals A1 to A19 below

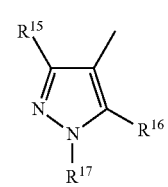

A1

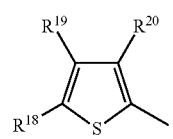

A2

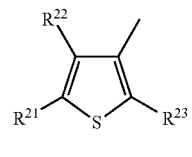

A3

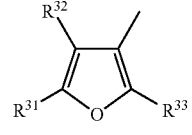

A9

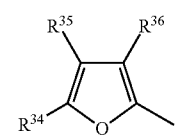

A10

-continued

A11

[structure: thiazole with R38, R37]

A12

[structure: thiazole with R39, R40]

A13

[structure: isothiazole with R41]

A14

[structure: oxazole with R42, R43]

A15

[structure: dihydrofuran with R44]

A18

[structure: pyrrole with R47, R48, R49, R50]

A19

[structure: thiadiazole with R51]

$R^{15}$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-halo-alkylthio having in each case 1 to 5 halogen atoms, aminocarbonyl or amino-carbonyl-$C_1$-$C_4$-alkyl, $R^{16}$ represents hydrogen, halogen, cyano, $C_1$-$C_4$-alkyl, $C_1$-$C_4$-alkoxy or $C_1$-$C_4$-alkylthio, $R^{17}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, $R^{18}$ and $R^{19}$ independently of one another, represent hydrogen, halogen, $C_1$-$C_4$-alkyl or $C_1$-$C_4$-haloalkyl having 1 to 5 halogen atoms, $R^{20}$ represents halogen, cyano or $C_1$-$C_4$-alkyl, or $C_1$-$C_4$-haloalkyl or $C_1$-$C_4$-haloalkoxy having in each case 1 to 5 halogen atoms, $R^{21}$ and $R^{22}$ independently of one another represent hydrogen, halogen, $C_1$-$C_4$-alkyl or $C_1$-$C_4$-haloalkyl having 1 to 5 halogen atoms, $R^{23}$ represents hydrogen, halogen, $C_1$-$C_4$-alkyl or $C_1$-$C_4$-haloalkyl having 1 to 5 halogen atoms, $R^{31}$ and $R^{32}$ independently of one another represent hydrogen, halogen, amino, $C_1$-$C_4$-alkyl or $C_1$-$C_4$-haloalkyl having 1 to 5 halogen atoms, $R^{33}$ represents hydrogen, halogen, $C_1$-$C_4$-alkyl or $C_1$-$C_4$-haloalkyl having 1 to 5 halogen atoms, $R^{34}$ and $R^{35}$ independently of one another represent hydrogen, halogen, amino, nitro, $C_1$-$C_4$-alkyl or $C_1$-$C_4$-haloalkyl having 1 to 5 halogen atoms, $R^{36}$ represents hydrogen, halogen, $C_1$-$C_4$-alkyl or $C_1$-$C_4$-haloalkyl having 1 to 5 halogen atoms, $R^{37}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{38}$ represents halogen, $C_1$-$C_4$-alkyl or $C_1$-$C_4$-haloalkyl having 1 to 5 halogen atoms, $R^{39}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{40}$ represents halogen, $C_1$-$C_4$-alkyl or $C_1$-$C_4$-haloalkyl having 1 to 5 halogen atoms, $R^{41}$ represents halogen, $C_1$-$C_4$-alkyl or $C_1$-$C_4$-haloalkyl having 1 to 5 halogen atoms, $R^{42}$ represents hydrogen or $C_1$-$C_4$-alkyl, $R^{43}$ represents halogen or $C_1$-$C_4$-alkyl, $R^{44}$ represents $C_1$-$C_4$-alkyl or $C_1$-$C_4$-haloalkyl having 1 to 5 halogen atoms, $R^{47}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{48}$ represents hydrogen, halogen, $C_1$-$C_4$-alkyl or $C_1$-$C_4$-haloalkyl having 1 to 5 halogen atoms, $R^{49}$ represents hydrogen, halogen, cyano, $C_1$-$C_4$-alkyl or $C_1$-$C_4$-haloalkyl having 1 to 5 halogen atoms, $R^{50}$ represents hydrogen, halogen, $C_1$-$C_4$-alkyl or $C_1$-$C_4$-haloalkyl having 1 to 5 halogen atoms, $R^{51}$ represents $C_1$-$C_4$-alkyl.

* * * * *